(12) United States Patent
Di Francesco et al.

(10) Patent No.: US 10,894,052 B2
(45) Date of Patent: Jan. 19, 2021

(54) HETEROCYCLIC INHIBITORS OF ATR KINASE

(71) Applicants: Board of Regents, The University of Texas System, Austin, TX (US); ChemPartner Corporation, South San Francisco, CA (US)

(72) Inventors: Maria Emilia Di Francesco, Houston, TX (US); Philip Jones, Houston, TX (US); Christopher Lawrence Carroll, Houston, TX (US); Suyambu Kesava Vijayan Ramaswamy, Houston, TX (US); Zhijun Kang, Richmond, TX (US); Michael Garrett Johnson, San Francisco, CA (US); Sarah Lively, San Carlos, CA (US); David Lapointe, Oakland, CA (US)

(73) Assignees: Board of Regents, The University of Texas System, Austin, TX (US); ChemPartner Corporation, South San Francisco, CA (US)

( * ) Notice: Subject to any disclaimer, the term of this patent is extended or adjusted under 35 U.S.C. 154(b) by 0 days.

(21) Appl. No.: 16/356,450

(22) Filed: Mar. 18, 2019

(65) Prior Publication Data

US 2019/0282584 A1 Sep. 19, 2019

Related U.S. Application Data

(60) Provisional application No. 62/644,189, filed on Mar. 16, 2018.

(51) Int. Cl.
*C07D 413/14* (2006.01)
*C07D 471/04* (2006.01)
*A61K 31/5377* (2006.01)
*A61P 35/00* (2006.01)

(52) U.S. Cl.
CPC .......... *A61K 31/5377* (2013.01); *A61P 35/00* (2018.01); *C07D 413/14* (2013.01); *C07D 471/04* (2013.01)

(58) Field of Classification Search
CPC .......................... C07D 413/14; C07D 471/04
See application file for complete search history.

(56) References Cited

U.S. PATENT DOCUMENTS

| | | | |
|---|---|---|---|
| 9,695,171 B2 | 7/2017 | Galatsis | |
| 10,392,376 B2 | 8/2019 | Di Francesco | |
| 10,421,765 B2 | 9/2019 | Di Francesco | |
| 10,745,420 B2 | 8/2020 | Di Francesco | |
| 10,800,769 B2 | 10/2020 | Di Francesco | |
| 10,800,774 B2 | 10/2020 | Di Francesco | |
| 2008/0292588 A1 | 11/2008 | Zhou | |
| 2009/0233926 A1 | 9/2009 | Butterworth | |
| 2010/0256143 A1 | 10/2010 | Baker | |
| 2011/0201599 A1 | 8/2011 | Bahceci | |
| 2012/0035407 A1 | 2/2012 | Charrier | |
| 2014/0315902 A1 | 10/2014 | Sun | |
| 2016/0287604 A1 | 10/2016 | Wortmann | |
| 2018/0370990 A1 | 12/2018 | Di Francesco | |
| 2019/0055240 A1 | 2/2019 | Di Francesco | |
| 2019/0367536 A1 | 12/2019 | Di Francesco | |
| 2020/0102296 A1 | 4/2020 | Di Francesco | |

FOREIGN PATENT DOCUMENTS

| | | |
|---|---|---|
| WO | 2007080382 | 7/2007 |
| WO | 2008023159 | 2/2008 |
| WO | 2008125833 | 10/2008 |
| WO | 2009007748 | 1/2009 |
| WO | 2009007750 | 1/2009 |
| WO | 2009007751 | 1/2009 |
| WO | 2009110510 | 9/2009 |
| WO | 2010073034 | 7/2010 |
| WO | 2010120996 | 10/2010 |
| WO | 2011062253 | 5/2011 |
| WO | 2011103715 | 9/2011 |
| WO | 2011106276 | 9/2011 |
| WO | 2011107585 | 9/2011 |
| WO | 2011154737 | 12/2011 |
| WO | 2012004299 | 1/2012 |
| WO | 2012147890 | 11/2012 |
| WO | 2014089379 | 6/2014 |
| WO | 2015085132 | 6/2015 |
| WO | 2015187451 | 12/2015 |
| WO | 2016020320 | 2/2016 |
| WO | 2016061097 | 4/2016 |
| WO | 2017210545 | 12/2017 |
| WO | 2018218197 | 11/2018 |
| WO | 2019036641 | 2/2019 |
| WO | 2019178590 | 9/2019 |

OTHER PUBLICATIONS

Cancer [online], Retrieved from the Internet, URL: http://www.nlm.nih.gov/medlineplus/cancer.html on Jul. 6, 2007; (2007).
Golub, T. et al., "Molecular Classification of Cancer: Class Discovery and Class Prediction by Gene Expression Monitoring", Science, 286(5439):531-7, (1999).
International Application No. PCT/US2018/034729; International Preliminary Report on Patentability, dated Nov. 26, 2019; 6 pages.
Lala, P. et al., "Role of Nitric Oxide in Tumor Progression: Lessons From Experimental Tumors", Cancer Metastasis Rev., 17(1):91-106, (1998).
U.S. Appl. No. 15/990,283; Non-Final Office Action, dated Dec. 26, 2018; 22 pages.
Barsanti, P. et al., "Structure-Based Drug Design of Novel Potent and Selective Azabenzimidazoles (ABI) as ATR Inhibitors", ACS Med Chem Lett., 6:42-6, (2015).

(Continued)

*Primary Examiner* — Shawquia Jackson
(74) *Attorney, Agent, or Firm* — Dennis A. Bennett; Cynthia Hathaway; John Desper

(57) ABSTRACT

The present disclosure relates to heterocyclic compounds and methods which inhibit ATR kinase to treat or prevent cancer.

32 Claims, No Drawings

(56) References Cited

OTHER PUBLICATIONS

Barsanti, P. et al., "Structure-Based Drug Design of Novel Potent and Selective Tetrahydropyrazolo[1,5-a] pyrazines as ATR Inhibitors", ACS Med Chem Lett., 6(1):37-41, (2015).
Bass, T. et al., "ETAA1 acts at stalled replication forks to maintain genome integrity", Nat Cell Biol, 18(11):1185-95, (25 page document), (2016).
Charrier, J. et al., "Discovery of Potent and Selective Inhibitors of Ataxia Telangiectasia Mutated and Rad3 Related (ATR) Protein Kinase as Potential Anticancer Agents", J Med Chem., 54(7):2320-30, (2011).
Choi, M. et al., "ATM Mutations in Cancer: Therapeutic Implications", Mol Cancer Ther, 15(8):1781-91, (2016).
Coburn, C. et al., "Discovery of a pharmacologically active antagonist of the two-pore-domain potassium channel K2P9.1 (TASK-3)", Chem. Med. Chem., 7(1):123-33, (2012).
Foote, K.M. et al., "Discovery of 4-{4-[(3R)-3-Methylmorpholin-4-yl]-6-[1-(methylsulfonyl)cyclopropyl]pyrimidin-2-yl}-1H-indole (AZ20): A Potent and Selective Inhibitor of ATR Protein Kinase with Monotherapy in Vivo Antitumor Activity", J Med Chem., 56(5):2125-38, (2013).
International Application No. PCT/US2018/034729; International Search Report and Written Opinion of the International Searching Authority, dated Nov. 9, 2018; 9 pages.
International Application No. PCT/US2018/042128 International Search Report and Written Opinion of the International Authority, dated Oct. 30, 2018; 10 pages.
International Application No. PCT/US2018/046937; International Search Report and Written Opinion of the International Searching Authority, dated Jan. 9, 2019; 9 pages.
International Application No. PCT/US2019/022727; International Search Report and Written Opinion of the International Searching Authority, dated May 14, 2019; 8 pages.
Karnitz, L. et al., "Molecular Pathways: Targeting ATR in Cancer Therapy", Clin Cancer Res, 21(21):4780-5, (2015).
Kwok, M. et al., "ATR Inhibition Induces Synthetic Lathality and Overcomes Chemoresistance in TP53- or ATM-Defective Chronic Lymphocytic Leukemia Cells", Blood, 127(5):582-96, (2015).
Menezes, D. et al., "A Synthetic Lethal Screen Reveals Enhanced Sensitivity to ATR Inhibitor Treatment in Mantle Cell Lymphoma with ATM Loss-of-Function", Mol Cancer Res., 13(1):120-9, (2015).
Mohni, K. et al., "ATR Pathway Inhibition Is Synthetically Lethal in Cancer Cells with ERCC1 Deficiency", Cancer Res., 74:2835-45, (2014).
Pubchem 53541968, 6-[4-(Morpholin-4-yl)-5H,6H,7H,8H-pyrido[4,3-d]pyrimidin-6-yl]pyridine-3-carbonitrile, Created on Dec. 3, 2011 (Dec. 3, 2011) pp. 1-11.
Pubchem 79023842, 4-Phenyl-5,6,7,8-tetrahydropyrido[4,3-d]pyrimidine, deposited on Oct. 19, 2014 (Oct. 19, 2014) pp. 1-10.
Toledo, L. et al., "A Cell-Based Screen Identifies ATR Inhibitors with Synthetic Lethal Properties for Cancer-Associated Mutations", Nat Struct Mol Biol, 18(6):721-7, (2011).
U.S. Appl. No. 16/104,561; Non-Final Office Action, dated Apr. 22, 2019; 26 pages.
U.S. Appl. No. 15/990,283; Notice of Allowance, dated May 13, 2019; 13 pages.
U.S. Appl. No. 16/035,310; Corrected Notice of Allowability, dated Jun. 3, 2019; 10 pages.
U.S. Appl. No. 16/035,310; Examiner-Initiated Interview Summary, dated Apr. 11, 2019; 1 page.
U.S. Appl. No. 16/035,310; Notice of Allowance, dated Apr. 11, 2019; 10 pages.
U.S. Appl. No. 16/507,851, filed Jul. 10, 2019; 256 pages.
International Application No. PCT/US2018/046937; International Preliminary Report on Patentability, dated Feb. 27, 2020; 6 pages.
U.S. Appl. No. 16/104,561; Examiner-Initiated Interview Summary, dated May 26, 2020; 1 page.
U.S. Appl. No. 16/104,561; Final Office Action, dated Feb. 24, 2020; 7 pages.
U.S. Appl. No. 16/104,561; Non-Final Office Action, dated Apr. 22, 2019; 33 pages.
U.S. Appl. No. 16/104,561; Notice of Allowance, dated May 26, 2020; 20 pages.
U.S. Appl. No. 16/507,851; Examiner-Initiated Interview Summary, dated Feb. 20, 2020; 1 page.
U.S. Appl. No. 16/507,851; Non-Final Office Action, dated Feb. 20, 2020; 11 pages.
U.S. Appl. No. 16/507,851; Notice of Allowance, dated Jun. 2, 2020; 22 pages.
U.S. Appl. No. 16/539,693; Non-Final Office Action, dated Jan. 16, 2020; 7 pages.
U.S. Appl. No. 16/539,693; Notice of Allowance, dated Apr. 23, 2020; 23 pages.
U.S. Appl. No. 16/539,693; Supplemental Notice of Allowability, dated Jun. 11, 2020; 7 pages.

HETEROCYCLIC INHIBITORS OF ATR KINASE

This application claims the benefit of priority of U.S. Provisional Application No. 62/644,189, filed Mar. 16, 2018, the disclosure of which is hereby incorporated by reference as if written herein in its entirety.

Disclosed herein are new heterocyclic compounds and compositions and their application as pharmaceuticals for treating disease. Methods of inhibition of ATR kinase activity in a human or animal subject are also provided for the treatment diseases such as cancer.

Ataxia-telangiectasia and Rad3-related kinase (ATR) is a member of the phosphatidylinositol 3-kinase-related protein kinase (PIKK) family, which also includes ataxia telangiectasia mutated (ATM) kinase, DNA-dependent protein kinase (DNA-PK), suppressor of morphogenesis in genitalia-1 (SMG-1), mammalian target of rapamycin (mTOR) and transformation/transcription associated protein (TRAPP). ATR and ATM are key regulators of the cellular DNA damage response (DDR) pathways, and are involved in maintaining the genome integrity in response to DNA-damage. Several distinct types of DNA lesions can occur because of diverse damaging events, including errors in normal replication processing, exposure to ionizing radiations (IR) and genotoxic agents, and different mechanisms of DNA repair have evolved to resolve specific kinds of DNA damage.

ATM is activated mainly by double-stranded DNA breaks (DSB), which may arise from collapsing of stalled replication forks or from exposure to IR. ATM has a key role in the activation of the G1/S checkpoint, which prevents cells with DNA damage to enter the S-phase, and allows DNA repair prior to the start of DNA replication. The effect is mediated primarily through the phosphorylation of two of the main downstream targets of ATM, CHK2 kinase and the tumor suppressor p53.

In turn, ATR is activated mainly in response to single stranded DNA breaks (SSB), that are found at stalled replication forks or are derived from DNA end-resection following processing of DNA DSBs. Replication protein A (RPA) binds to the DNA single strands, the ATR-interacting protein (ATRIP) binds then to the RPA-coated DNA strands and recruits ATR to the SSB damage site. Recruitment of additional protein components to the complex results in activation of ATR kinase, followed by phosphorylation and activation of its downstream effectors, including CHK1 kinase. Activation of ATR results in slow replication origin firing, stabilization of the stalled replication forks which prevents their collapse into DSBs, and restart of fork replication once the damage is repaired. The ATR/CHK1 pathway is a major regulator of the G2/M checkpoint, which prevents the premature entry of cells into mitosis in the presence of incomplete DNA replication and/or DNA damage (reviewed in M. J. O'Connor, Molecular Cell, 2015, 60, November 19, p. 547-560; A. M. Weber et al., *Pharmacology and Therapeutics* 2015, 149, 124-138).

Because of the critical role of ATR in DDR, pharmacological inhibition of ATR may be an effective cancer treatment in many specific settings. Indeed, several cancers (e.g. oncogene-driven tumors) are characterized by higher levels of replication stress compared to normal cells, and blockade of ATR can increase their genomic instability and induce substantial cell death (O. Gilad et al., *Cancer Res.* 70, 9693-9702, 2010). Moreover, most cancers are characterized by loss or deregulation of one or more DDR pathways, resulting in increased genomic instability and greater dependency on remaining DDR pathways for survival. For example, a cancer cell that has a defective G1 checkpoint because of mutations in p53, will rely more on the G2/M checkpoints to allow DNA repair and cell survival. Inhibition of ATR, a key regulator of the G2/M checkpoints, can result in complete loss of DNA damage checkpoints, ultimately leading to accumulation of DNA damage and mitotic catastrophe. Normal cells, with a functioning G1 checkpoint, would be less affected by pharmacological inhibition of ATR. Similarly, in cancer cells harboring ATM-deficiency, ATR inhibition results in a synthetic lethality dependency, leading to increased sensitivity and preferential killing. Therefore, ATR inhibition could be used for treatment of tumors with deficient ATM and/or p53 function (P. M. Reaper, M. R. Griffiths et al., *Nature Chem. Bio.* 7, 428-430, 2011)

Additional potential synthetic lethality interactions between ATR and other components of the DDR pathway have been reported, and might be exploited by treatment with ATR inhibitors, including treatment of cancers characterized by loss/deficiency of XRCC 1, ERCC1, MRE11 and other components if the MRN complex (reviewed in A. M. Weber et al., *Pharmacology and Therapeutics* 2015, 149, 124-138). Recently, a synthetic lethality dependency has been reported for ATR inhibition in tumors deficient for ARID A, a member of the SWI/SNF chromatin-remodeling complex frequently mutated in human cancer (C. T. Williamson et al., *Nature Communications,* 2016, 7, 13837).

ATR inhibition can be exploited for treatment of cancer also in combination with DNA-damaging therapeutic agents, such as radiotherapy and chemotherapy. Widely used chemotherapics include antimetabolites (e.g. gemcitabine), DNA crosslinking agents such as platinum salts, alkylating agents (e.g. temozolomide) and inhibitors of topoisomerase (e.g. camptothecin, topotecan, irinotecan). Administration of these agents and/or ionizing radiation results in a variety of DNA lesions that ultimately bring the cancer cells towards mitotic catastrophe and cell death. In cancer cells treated with such agents, inhibition of ATR signaling can prevent DNA damage repair, thus further reducing the often already compromised abilities of cancer cells to respond to the induced replication stress, and hence potentiating the effectiveness of the above treatments.

An additional opportunity to leverage ATR inhibition in combination therapy is together with other DDR agents, for example in combination with inhibitors of Poly ADP ribose polymerase (PARP). PARP inhibitors prevent the repair of single strand DNA breaks, resulting into formation of DNA double strand breaks. In the context of cancers that are deficient in the homologous recombination (HR) DNA repair pathway, such as BRCA 1/2 mutant cancers, PARP inhibition has proven clinically efficacious. Recent reports highlight that targeting critical cell-cycle checkpoints at the same time—for example by combining a PARP inhibitor with an ATR inhibitor—results in increased sensitivity to PARP inhibition and in significant efficacy in several preclinical cancer models, including PARP inhibitor resistant patient derived models. These findings highlight the potential clinical applications of ATR inhibition in combination with other DDR inhibitors, and the field is likely to expand to several other combination opportunities beyond PARP inhibitors (H. Kim et al., *Clinical Cancer Research*, April 2017, DOI:10.1158/1078-0432.CCR-16-2273; A. Y. K. Lau et al., AACR National Meeting 2017, Abstract 2494/25, ATR inhibitor AZD6738 as monotherapy and in combination with olaparib or chemotherapy: defining pre-clinical dose-schedules and efficacy modelling).

Thus, disclosed herein are methods for treating cancers using ATR inhibitors, cancers characterized by elevated levels of replication stress, defective in cell cycle checkpoints, or harboring defects in cellular DNA damage repair pathways, such as deficiency in the ATM/p53 pathway or additional synthetic lethality dependencies with other DDR components. Also disclosed herein are methods using ATR inhibitors to treat cancers that are mutated/defective in ARID 1A, or are mutated/defective in cellular pathways that are in a synthetic lethal dependency with the ATR pathway. Disclosed herein are also methods for treatment of cancer using ATR inhibitors in combination with radiation, with DNA damaging chemotherapeutic agents, and with other DDR inhibitors, including PARP inhibitors.

Furthermore, inhibition of ATR offers an opportunity for treatment of certain cancers associated with the regulation of telomere length. Telomeres are nucleoprotein complexes comprising both hexanucleotide DNA repeat sequences and telomere-associated proteins, which act to stabilize the ends of chromosomes. In normal somatic cells, shortening of the telomeres over time leads to senescence or apoptosis, and this action can act as an upper limit on cellular life span. In most advanced cancers, the enzyme telomerase is activated, whose role is to add a repeat sequence to the 3' end of the DNA, thus reversing the telomere shortening process and increasing the cellular lifespan. Thus, activation of telomerase has been invoked in cancer cell immortalization. A second, telomerase-independent mechanism for maintaining telomeres, termed Alternate Lengthening of Telomers (ALT), has been implicated in approximately 5% of all human cancers, and it is prevalent in specific kinds of cancer, including osteosarcoma and glioblastoma. ALT is enriched in mesenchymal-originating tumors, and is usually associated with decreased survival rates. Studies revealed that ATR kinase is functionally required for ALT, and that ALT cells are more sensitive to ATR inhibition (R. L. Flynn, K. E. Cox, *Science* 2015, 347 (6219), 273-277).

There is a need for therapies having efficacy towards ALT-positive cancers. The ALT pathway is poorly understood, and cancers that feature ALT are resistant to the action of telomerase inhibitors. Thus, described herein are methods for treating cancers, ALT-positive types of cancers, using ATR inhibitors.

Disclosed herein are novel compounds and pharmaceutical compositions, certain of which have been found to inhibit ATR kinase, together with methods of synthesizing and using the compounds, including methods for treating ATR kinase-mediated diseases in a patient by administering the compounds.

In certain embodiments, compounds have structural Formula (I):

or a salt thereof, wherein:

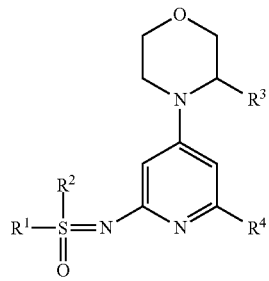

$R^1$ and $R^2$ are independently chosen from $C_{1-4}$ alkyl, $C_{1-4}$ haloalkyl, $C_{3-6}$ cycloalkyl, $C_{3-6}$ heterocycloalkyl, aryl, and heteroaryl, each of which is optionally substituted with one or more $R^5$ groups, or $R^1$ and $R^2$, together with the sulfur to which they are both attached, form a heterocycloalkyl ring which is optionally substituted with one or more $R^5$ groups;

$R^3$ is chosen from hydrogen, $C_{1-6}$ alkyl, and $C_{1-6}$ haloalkyl;

$R^4$ is chosen from $C_{5-10}$ aryl and 5-10 membered heteroaryl, each of which is optionally substituted with one or more $R^6$ groups;

each $R^5$ is independently chosen from $NR^8R^9$, halogen, cyano, hydroxy, oxo, alkyl, haloalkyl, cycloalkyl, heterocycloalkyl, hydroxyalkyl, $OR^8$, $NR^7C(O)R^8$, $NR^7C(O)OR^8$, $NR^7C(O)NR^8R^9$, $C(O)R^8$, $C(O)OR^8$, and $C(O)NR^8R^9$;

each $R^6$ is independently chosen from $NR^{11}R^{12}$, halogen, cyano, hydroxy, oxo, alkyl, haloalkyl, cycloalkyl, heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

each $R^7$, $R^8$ and $R^9$ is independently chosen from hydrogen, $C_{1-4}$ alkyl, $C_{3-6}$ cycloalkyl, and heterocycloalkyl and is optionally substituted with halo, hydroxy, $C_{1-3}$ alkyl, $C_{1-3}$ haloalkyl, and $C_{1-3}$ alkoxy; or any two of $R^7$, $R^8$ and $R^9$, together with the atom to which they are both attached, can form a 3-7 membered cycloalkyl or heterocycloalkyl ring; and each $R^{10}$, $R^{11}$ and $R^{12}$ is independently chosen from hydrogen, $C_{1-4}$ alkyl, $C_{3-6}$ cycloalkyl, and heterocycloalkyl and is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

Certain compounds disclosed herein may possess useful ATR kinase inhibiting activity, and may be used in the treatment or prophylaxis of a disease or condition in which ATR kinase plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting ATR kinase. Other embodiments provide methods for treating an ATR kinase-mediated disorder in a patient in need of such treatment, comprising administering to the patient a therapeutically effective amount of a compound or composition according to the present disclosure. Also provided is the use of certain compounds disclosed herein for use in the manufacture of a medicament for treating a disease or condition ameliorated by the inhibition of ATR kinase.

In certain embodiments, compounds have structural Formula (II):

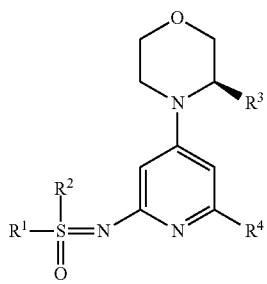

(II)

or a salt thereof, wherein:
R$^1$ and R$^2$ are independently chosen from C$_{1-4}$ alkyl, C$_{1-4}$ haloalkyl, C$_{3-6}$ cycloalkyl, C$_{3-6}$ heterocycloalkyl, aryl, and heteroaryl, each of which is optionally substituted with one or more R$^5$ groups, or R$^1$ and R$^2$, together with the sulfur to which they are both attached, form a heterocycloalkyl ring which is optionally substituted with one or more R$^5$ groups;
R$^3$ is chosen from hydrogen, C$_{1-6}$ alkyl, and C$_{1-6}$ haloalkyl;
R$^4$ is chosen from C$_{5-10}$ aryl and 5-10 membered heteroaryl and is optionally substituted with one or more R$^6$ groups;
each R$^5$ is independently chosen from NR$^8$R$^9$, halogen, cyano, hydroxy, oxo, alkyl, haloalkyl, cycloalkyl, heterocycloalkyl, hydroxyalkyl, OR$^8$, NR$^7$C(O)R$^8$, NR$^7$C(O)OR$^8$, NR$^7$C(O)NR$^8$R$^9$, C(O)R$^8$, C(O)OR$^8$, and C(O)NR$^8$R$^9$;
each R$^6$ is independently chosen from NR$^{11}$R$^{12}$, halogen, cyano, hydroxy, oxo, alkyl, haloalkyl, cycloalkyl, heterocycloalkyl, hydroxyalkyl, OR$^{11}$, NR$^{10}$C(O)R$^{11}$, NR$^{10}$C(O)OR$^{11}$, NR$^{10}$C(O)NR$^{11}$R$^{12}$, C(O)R$^{11}$, C(O)OR$^{11}$, and C(O)NR$^{11}$R$^{12}$;
each R$^7$, R$^8$ and R$^9$ is independently chosen from hydrogen, C$_{1-4}$alkyl, C$_{3-6}$ cycloalkyl and heterocycloalkyl and is optionally substituted with halo, hydroxy, C$_{1-3}$ alkyl, C$_{1-3}$ haloalkyl and C$_{1-3}$alkoxy; or any two of R$^7$, R$^8$ and R$^9$, together with the atom to which they are both attached can form a 3-7 membered cycloalkyl or heterocycloalkyl ring; and
each R$^{10}$, R$^{11}$ and R$^{12}$ is independently chosen from hydrogen, C$_{1-4}$ alkyl, C$_{3-6}$ cycloalkyl and heterocycloalkyl and is optionally substituted with one or more groups chosen from halo, hydroxy and alkoxy; or any two of R$^{10}$, R$^{11}$ and R$^{12}$, together with the atom to which they are both attached, can form a 3-7 membered cycloalkyl or heterocycloalkyl ring.

In certain embodiments, R$^1$ and R$^2$ are independently chosen from C$_{1-4}$ alkyl, C$_{1-4}$ haloalkyl, C$_{3-6}$ cycloalkyl, C$_{3-6}$ heterocycloalkyl, aryl, and heteroaryl and are optionally substituted with one or two R$^5$ groups, or R$^1$ and R$^2$, together with the sulfur to which they are both attached, forms a heterocycloalkyl ring which is optionally substituted with one or two R$^5$ groups.

In certain embodiments, R$^1$ and R$^2$ are independently chosen from C$_{1-4}$ alkyl, C$_{1-4}$haloalkyl, C$_{3-6}$ cycloalkyl, C$_{3-6}$ heterocycloalkyl, aryl, and heteroaryl, each of which is optionally substituted with one or two R$^5$ groups.

In certain embodiments, R$^1$ and R$^2$ are independently chosen from C$_{1-4}$ alkyl and C$_{3-6}$cycloalkyl, each of which is optionally substituted with one R$^5$ group.

In certain embodiments, R$^1$ and R$^2$ are independently chosen from C$_{1-4}$ alkyl and C$_{3-6}$ cycloalkyl.

In certain embodiments, R$^1$ and R$^2$, together with the sulfur to which they are both attached, form a heterocycloalkyl ring which is optionally substituted with one or two R$^5$ groups.

In certain embodiments, R$^1$ and R$^2$, together with the sulfur to which they are both attached, form a heterocycloalkyl ring which is optionally substituted with one R$^5$ group.

In certain embodiments, R$^1$ and R$^2$, together with the sulfur to which they are both attached, form a heterocycloalkyl ring.

In certain embodiments, R$^1$ and R$^2$, together with the sulfur to which they are both attached and the nitrogen and oxygen to which the sulfur is attached, is a group Z chosen from

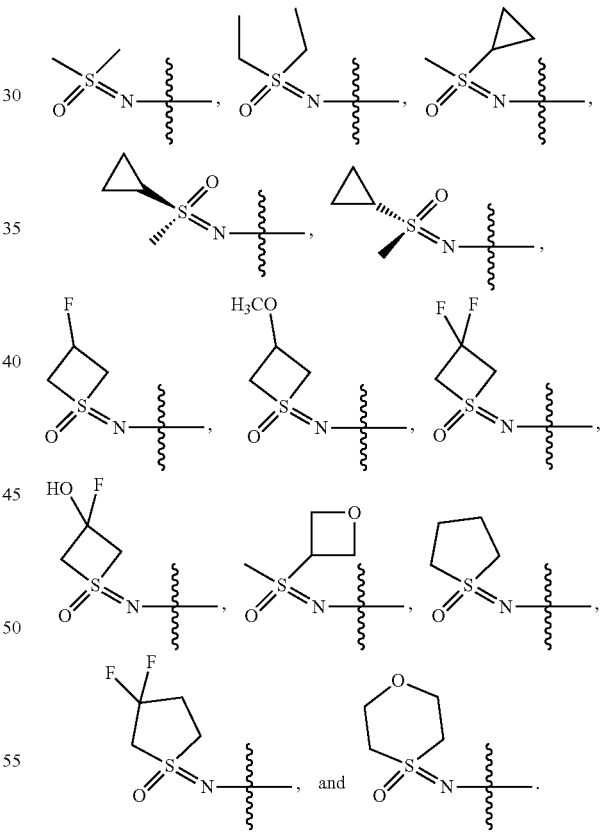

In certain embodiments, R$^3$ is C$_{1-6}$ alkyl.
In certain embodiments, R$^3$ is methyl.
In certain embodiments, R$^4$ is 5-10 membered heteroaryl and is optionally substituted with one or more R$^6$ groups.
In certain embodiments, R$^4$ is chosen from indole, pyrrolopyridine, pyrazolopyridine, imidazolopyridine, pyrrolopyrazine, pyrazolopyrazine, pyrrolopyrimidine, pyrazolopyrimidine, imidazolopyrimidine, pyrrolopyridazine, pyrazolopyridazine, and imidazolopyridazine, and is optionally substituted with one or more $R^6$ groups.

In certain embodiments, $R^4$ is chosen from indole, pyrrolopyridine, pyrazolopyridine, pyrrolopyrazine, pyrazolopyrazine, pyrrolopyrimidine, pyrazolopyrimidine, pyrrolopyridazine, and pyrazolopyridazine, and is optionally substituted with one or more $R^6$ groups.

In certain embodiments, $R^4$ is chosen from 3H-imidazo[4,5-b]pyridine, 1H-imidazo[4,5-c]pyridazine, purine, and 1H-imidazo[4,5-b]pyrazine and is optionally substituted with one, two, or three $R^6$ groups.

In certain embodiments, $R^4$ is chosen from 1H-pyrrolo[2,3-b]pyridine, 7H-pyrrolo[2,3-c]pyridazine, 7H-pyrrolo[2,3-d]pyrimidine, and 5H-pyrrolo[2,3-b]pyrazine and is optionally substituted with one, two, or three $R^6$ groups.

In certain embodiments, $R^4$ is 1H-pyrrolo[2,3-b]pyridine and is optionally substituted with one or two $R^6$ groups.

In certain embodiments, $R^4$ is chosen from optionally substituted N

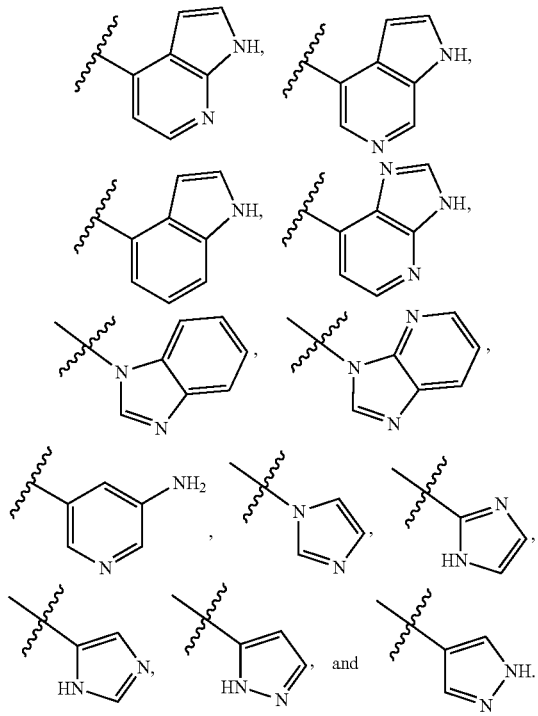

In certain embodiments, each $R^5$ is independently chosen from $NR^8R^9$, halogen, cyano, hydroxy, oxo, alkyl, haloalkyl, cycloalkyl, heterocycloalkyl, hydroxyalkyl, $OR^8$, $NR^7C(O)R^8$, $NR^7C(O)OR^8$, $NR^7C(O)NR^8R^9$, $C(O)R^8$, $C(O)OR^8$, and $C(O)NR^8R^9$.

In certain embodiments, each $R^5$ is independently chosen from $C(O)R^8$, $C(O)OR^8$, and $C(O)NR^8R^9$.

In certain embodiments, each $R^5$ is independently chosen from $C(O)R^8$ and $C(O)OR^8$.

In certain embodiments, each $R^6$ is independently chosen from $NR^{11}R^{12}$, halogen, cyano, hydroxy, oxo, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$.

In certain embodiments, each $R^6$ is independently chosen from $NR^{11}R^{12}$, halogen, cyano, hydroxy, and oxo.

In certain embodiments, each $R^6$ is independently chosen from halogen and cyano.

In certain embodiments of the present disclosure, compounds have structural Formula (III):

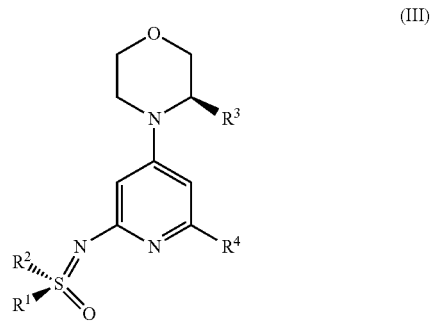

(III)

or a salt thereof, wherein:
$R^1$ and $R^2$ are independently chosen from $C_{1-4}$ alkyl, $C_{1-4}$ haloalkyl, $C_{3-6}$ cycloalkyl, $C_{3-6}$ heterocycloalkyl, aryl, and heteroaryl, each of which is optionally substituted with one or more $R^5$ groups, or $R^1$ and $R^2$, together with the sulfur to which they are both attached, form a heterocycloalkyl ring which is optionally substituted with one or more $R^5$ groups;

$R^3$ is chosen from hydrogen, $C_{1-6}$ alkyl, and $C_{1-6}$ haloalkyl;

$R^4$ is chosen from $C_{5-10}$ aryl and 5-10 membered heteroaryl and is optionally substituted with one or more $R^6$ groups;

each $R^5$ is independently chosen from $NR^8R^9$, halogen, cyano, hydroxy, oxo, alkyl, haloalkyl, cycloalkyl, heterocycloalkyl, hydroxyalkyl, $OR^8$, $NR^7C(O)R^8$, $NR^7C(O)OR^8$, $NR^7C(O)NR^8R^9$, $C(O)R^8$, $C(O)OR^8$, and $C(O)NR^8R^9$;

each $R^6$ is independently chosen from $NR^{11}R^{12}$, halogen, cyano, hydroxy, oxo, alkyl, haloalkyl, cycloalkyl, heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

each $R^7$, $R^8$ and $R^9$ is independently chosen from hydrogen, $C_{1-4}$ alkyl, $C_{3-6}$ cycloalkyl, and heterocycloalkyl and is optionally substituted with halo, hydroxy, $C_{1-3}$ alkyl, $C_{1-3}$ haloalkyl, and $C_{1-3}$ alkoxy; or any two of $R^7$, $R^8$ and $R^9$, together with the atom to which they are both attached can form a 3-7 membered cycloalkyl or heterocycloalkyl ring; and each $R^{10}$, $R^{11}$ and $R^{12}$ is independently chosen from hydrogen, $C_{1-4}$ alkyl, $C_{3-6}$ cycloalkyl, and heterocycloalkyl and is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

The present disclosure also relates to a method of inhibiting at least one ATR kinase function comprising the step of contacting ATR kinase with a compound as described herein. The cell phenotype, cell proliferation, activity of ATR kinase, change in biochemical output produced by active ATR kinase, expression of ATR kinase, or binding of ATR kinase with a natural binding partner may be monitored. Such methods may be modes of treatment of disease, biological assays, cellular assays, biochemical assays, or the like.

Also provided herein is a method of treating an ATR kinase-mediated disease comprising administering a therapeutically effective amount of a compound as disclosed herein, or a salt thereof, to a patient in need thereof.

In certain embodiments, the ATR kinase-mediated disease is a proliferative disease.

In certain embodiments, the proliferative disease is a myeloproliferative disorder.

In certain embodiments, the proliferative disease is cancer.

In certain embodiments, the cancer is lymphoma.

In certain embodiments, the cancer is B cell lymphoma.

In certain embodiments, the cancer is pancreatic cancer.

Also provided herein is a compound as disclosed herein for use as a medicament.

Also provided herein is a compound as disclosed herein for use as a medicament for treating an ATR kinase-mediated disease.

Also provided is the use of a compound as disclosed herein as a medicament.

Also provided is the use of a compound as disclosed herein as a medicament for treating an ATR kinase-mediated disease.

Also provided is a compound as disclosed herein for use in the manufacture of a medicament for treating an ATR kinase-mediated disease.

Also provided is the use of a compound as disclosed herein for treating an ATR kinase-mediated disease.

Also provided herein is a method of inhibition of ATR kinase comprising contacting ATR kinase with a compound as disclosed herein, or a salt thereof.

Also provided herein is a method for achieving an effect in a patient comprising administrating a therapeutically effective amount of a compound as disclosed herein, or a salt thereof, to a patient, wherein the effect is chosen from cognition enhancement.

Also provided is a method of modulation of an ATR kinase-mediated function in a subject comprising administrating a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

In certain embodiments, the pharmaceutical composition is formulated for parenteral administration.

DETAILED DESCRIPTION

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no margin of error, such as a standard deviation to a mean value given in a chart or table of data, is recited, the term "about" should be understood to mean that range which would encompass the recited value and the range which would be included by rounding up or down to that figure as well, considering significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH═CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl will comprise from 1 to 10 carbon atoms. In further embodiments, the alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl, "as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane. "Cycloalkyl," as used herein, alone or in combination, encompasses "bicycloalkyl," "bridged cycloalkyl," and "spirocycloalkyl," as defined below.

The term "bicycloalkyl," as used herein, alone or in combination, refers to a cyclic alkyl system that is characterized by the presence of two atoms, termed "bridgehead atoms" that are connected to each other via three bond pathways. "Bicycloalkyl" thus encompasses, by way of example, bicyclo[2.2.1]heptane, also known as norbornane, bicyclo[2.2.2]octane, bicyclo[2.2.0]hexane and bicyclo[3.3.0]octane.

The term "bridged cycloalkyl," as used herein, alone or in combination, refers to a bicycloalkyl system in which all three of the bond pathways between bridgehead atoms contain at least one atom. "Bridged cycloalkyl" thus encompasses, by way of example, bicyclo[2.2.1]heptane, also known as norbornane, and bicyclo[2.2.2]octane. "Bridged cycloalkyl" thus does not encompass bicyclo[2.2.0]hexane or bicyclo [3.3.0]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, the heteroaryl will comprise from 1 to 4 heteroatoms as ring members. In further embodiments, the heteroaryl will comprise from 1 to 2 heteroatoms as ring members. In certain embodiments, the heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each the heteroatom may be independently chosen from nitrogen, oxygen, and sulfur. In certain embodiments, the heterocycloalkyl will comprise from 1 to 4 heteroatoms as ring members. In further embodiments, the heterocycloalkyl will comprise from 1 to 2 heteroatoms as ring members. In certain embodiments, the heterocycloalkyl will comprise from 3 to 8 ring members in each ring. In further embodiments, the heterocycloalkyl will comprise from 3 to 7 ring members in each ring. In yet further embodiments, the heterocycloalkyl will comprise from 5 to 6 ring members in each ring. "Heterocycloalkyl" and "heterocycle" are intended to include sulfones, sulfoxides, sulfoximines, sulfimides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited. The term "heterocycloalkyl," as used herein, alone or in combination, is understood to encompass "heterobicycloalkyl" and "bridged heterocycloalkyl," as defined below.

The term "heterobicycloalkyl," as used herein, alone or in combination, refers to a heterocyclic alkyl system that is characterized by the presence of two atoms, termed "bridgehead atoms" that are connected to each other via three bond pathways. "Bicycloalkyl" thus encompasses, by way of example, bicyclo[2.2.1]heptane, also known as norbornane, bicyclo[2.2.2]octane, bicyclo[2.2.0]hexane and bicyclo[3.3.0]octane.

The term "bridged heterocycloalkyl," as used herein, alone or in combination, refers to a heterobicycloalkyl system in which all three of the bond pathways between bridgehead atoms contain at least one atom. "Bridged heterocycloalkyl" thus encompasses, by way of example, 1,4-diazabicyclo[2.2.2]octane, also known as DABCO, and 7-azabicyclo[2.2.1]heptane.

Bicyclic ring systems can be described using terminology that will be recognized by the person in the art. A bicyclic compound can be named as the fusion of two ring systems. For example, "benzobenzene" is understood to refer to naphthalene. Unless specifically restricted, any ring fusion isomer will be embraced by this terminology. For example, "benzonaphthalene" is understood to embrace both anthracene and phenanthrene. As a further example, pyrrolopyridine is understood to embrace any compound having pyrrole fused to pyridine, and thus embraces 4-azaindole, 5-azaindole, 6-azaindole, and 7-azaindole.

The term "heterobicycloalkyl," as used herein, alone or in combination, refers to a saturated, partially unsaturated, or fully unsaturated (but nonaromatic) cyclic alkyl system, containing at least one heteroatom as a ring member, that is characterized by the presence of two atoms, termed "bridgehead atoms" that are connected to each other via three bond pathways. "Heterobicycloalkyl" thus encompasses, by way of example, 7-azabicyclo[2.2.1]heptane, 1,4-diazabicyclo[2.2.2]octane, also referred to as "DABCO", 1-azabicyclo[2.2.0]hexane, and 3-azabicyclo[3.3.0]octane.

The term "bridged heterocycloalkyl," as used herein, alone or in combination, refers to a heterobicycloalkyl system in which all three of the bond pathways between bridgehead atoms contain at least one atom. "Bridged heterocycloalkyl" thus encompasses, by way of example, 7-azabicyclo[2.2.1]heptane, 1,4-diazabicyclo[2.2.2]octane, also referred to as "DABCO", but not 1-azabicyclo[2.2.0] hexane, or 3-azabicyclo[3.3.0]octane.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group. Examples of hydroxyalkyl groups include hydroxymethyl, 1-hydroxyethyl, 2-hydroxyethyl, and 2-hydroxy-2-propyl.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all the hydrogen atoms are replaced by halogen atoms.

The term "perhaloalkyl" as used herein, alone or in combination, refers to an alkyl group where all the hydrogen atoms are replaced by halogen atoms.

The term "spirocycloalkyl," as used herein, alone or in combination, refers to an alkyl group having two rings that has a single atom common to both rings. Examples of spirocycloalkyl systems include spiro[3.3]heptane and spiro[4.4]nonane.

The term "spiroheterocycloalkyl," as used herein, alone or in combination, refers to a heteroalkyl group having two rings that has a single atom common to both rings. Examples of spirocycloalkyl systems include 2-azaspiro[3.3]heptane and 3-azaspiro[4.4]nonane.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The term "sulfimide" refers to a RS(=NR')R" group with R, R', and R" as defined herein.

The term "sulfoximine" refers to a RS(=O)(=NR')R" group with R, R', and R" as defined herein.

The terms "thia" and "thio," as used herein, alone or in combination, refer to a —S-group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethylsilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a moiety may be defined as needed; in these cases, the optional substitution will be as defined, often immediately following the phrase, "optionally substituted with."

The term R or the term R', or the term R", appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R, R' and R" groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

The term "enantiomer," as used herein, alone or in combination, refers to one of a pair of compounds that differ in absolute stereochemistry at every stereocenter. Each enantiomer in a pair of compounds is thus the mirror image of the other enantiomer.

The term "epimer," as used herein, alone or in combination, refers to one of a pair of compounds that differ in absolute stereochemistry at a single stereocenter.

The term "diastereomer," as used herein, alone or in combination, refers to one of a pair of compounds that neither have identical stereochemistry nor are enantiomers of each other.

Asymmetric centers exist in the compounds disclosed herein. These centers are designated by the symbols "R" or "S," depending on the configuration of substituents around the chiral carbon atom. The invention encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

Certain of the compounds disclosed herein can exist as a mixture of two diastereomers. In some embodiments, the two diastereomers are present in equal amounts. In some embodiments, the compound contains 60% or more of the major diastereomer. In some embodiments, the compound contains 70% or more of the major diastereomer. In some embodiments, the compound contains 80% or more of the major diastereomer. In some embodiments, the compound contains 90% or more of the major diastereomer. In some embodiments, the compound contains 95% or more of the major diastereomer. In some embodiments, the compound contains 98% or more of the major diastereomer.

The term "bond" refers to a covalent linkage between two atoms, or two moieties when the atoms joined by the bond are part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means administrating two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"ATR kinase inhibitor" is used herein to refer to a compound that exhibits an $IC_{50}$ with respect to ATR kinase activity of no more than about 100 µM and more typically not more than about 50 µM, as measured in the ATR/ATRIP biochemical assay or in the ATR kinase pCHK1 cellular assay described generally herein. "$IC_{50}$" is that concentration of inhibitor which reduces to half-maximal level the activity of an enzyme (e.g., ATR kinase), or the ATR-induced phosphorylation of CHK1 at Serine 345 in cells. Certain compounds disclosed herein have been discovered to exhibit inhibition against ATR kinase. In certain embodiments, compounds will exhibit an $IC_{50}$ with respect to ATR kinase of no more than about 10 µM; in further embodiments, compounds will exhibit an $IC_{50}$ with respect to ATR kinase of no more than about 2 µM; in yet further embodiments, compounds will exhibit an IC50 with respect to ATR kinase of not more than about 1 µM; in yet further embodiments, compounds will exhibit an $IC_{50}$ with respect to ATR kinase of not more than about 500 nM; in yet further embodiments, compounds will exhibit an $IC_{50}$ with respect to ATR kinase of not more than about 200 nM; in yet further embodiments, compounds will exhibit an $IC_{50}$ with respect to ATR kinase of not more than about 100 nM, as measured in the ATR kinase assay described herein.

The phrase "therapeutically effective" is intended to qualify the amount of active ingredients used in treating a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Salts

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be used to prepare and purify the compound in question. Basic addition salts may also be formed and be pharmaceutically acceptable.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Formulations

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum Arabic, talc, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Preferred unit dosage formulations are those containing an effective dose, as herein below recited, or an appropriate fraction thereof, of the active ingredient.

In addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the mode of administration.

The compounds can be administered in various modes, e.g. orally, topically, or by injection. The precise amount of compound administered to a patient will be the responsibility of the attendant physician. The specific dose level for any patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Combinations and Combination Therapies

The compounds of the present disclosure can be used, alone or in combination with other pharmaceutically active compounds, to treat conditions such as those previously described hereinabove. The compound(s) of the present disclosure and other pharmaceutically active compound(s) can be administered simultaneously (either in the same dosage form or in separate dosage forms) or sequentially. Accordingly, in one embodiment, the present disclosure comprises methods for treating a condition by administering to the subject a therapeutically-effective amount of one or more compounds of the present disclosure and one or more additional pharmaceutically active compounds.

In another embodiment, there is provided a pharmaceutical composition comprising one or more compounds of the present disclosure, one or more additional pharmaceutically active compounds, and a pharmaceutically acceptable carrier.

In another embodiment, the one or more additional pharmaceutically active compounds is selected from anti-cancer drugs, anti-proliferative drugs, and anti-inflammatory drugs.

ATR inhibitor compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer an ATR inhibitor compound, as described herein, in combination with another therapeutic agent. By way of example only, the therapeutic effectiveness of an ATR inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is an ATR inhibitor as described herein) may be administered in any order, or simultaneously. If simultaneously, the multiple therapeutic agents are optionally provided in a single, unified form, or in multiple forms (by way of example only, either as a single pill or as two separate pills).

In another embodiment, an ATR inhibitor is optionally used in combination with procedures that provide additional benefit to the patient. An ATR inhibitor and any additional therapies are optionally administered before, during or after the occurrence of a disease or condition, and the timing of administering the composition containing an ATR inhibitor varies in some embodiments. Thus, for example, an ATR inhibitor is used as a prophylactic and is administered continuously to subjects with a propensity to develop conditions or diseases to prevent the occurrence of the disease or condition. An ATR inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. In some embodiments of the invention various alternatives to the embodiments described herein are employed in practicing the invention.

An ATR inhibitor can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases an ATR inhibitor may be optimally used together with one or more of the following non-limiting examples of anti-cancer agents:

1) inhibitors or modulators of a protein involved in one or more of the DNA damage repair (DDR) pathways such as:
   a. PARP1/2, including, but not limited to: olaparib, niraparib, rucaparib;
   b. checkpoint kinase 1 (CHK1), including, but not limited to: UCN-01, AZD7762, PF477736, SCH900776, MK-8776, LY2603618, V158411, and EXEL-9844;
   c. checkpoint kinase 2 (CHK2), including, but not limited to: PV1019, NSC 109555, and VRX0466617;
   d. dual CHK1/CHK2, including, but not limited to: XL-844, AZD7762, and PF-473336;
   e. WEE1, including, but not limited to: MK-1775 and PD0166285;
   f. ATM, including, but not limited to KU-55933,
   g. DNA-dependent protein kinase, including, but not limited to NU7441 and M3814; and
   h. Additional proteins involved in DDR;
2) Inhibitors or modulators of one or more immune checkpoints, including, but not limited to:
   a. PD-1 inhibitors such as nivolumab (OPDIVO), pembrolizumab (KEYTRUDA), pidilizumab (CT-011), and AMP-224 (AMPLIMMUNE);
   b. PD-L1 inhibitors such as Atezolizumab (TECENTRIQ), Avelumab (Bavencio), Durvalumab (Imfinzi), MPDL3280A (Tecentriq), BMS-936559, and MEDI4736;
   c. anti-CTLA-4 antibodies such as ipilimumab (YERVOY) and CP-675,206 (TREMELIMUMAB);
   d. inhibitors of T-cell immunoglobulin and mucin domain 3 (Tim-3);
   e. inhibitors of V-domain Ig suppressor of T cell activation (Vista);
   f. inhibitors of band T lymphocyte attenuator (BTLA);
   g. inhibitors of lymphocyte activation gene 3 (LAG3); and
   h. inhibitors of T cell immunoglobulin and immunoreceptor tyrosine-based inhibitory motif domain (TIGIT);
3) telomerase inhibitors or telomeric DNA binding compounds;
4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;
5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);
6) anti-metabolites, including, but not limited to: cladribine (LEUSTATIN), cytarbine, (ARA-C), mercaptupurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), and raltitrexed;
7) antimitotic, which are often plant alkaloids and terpenoids, or derivatives thereof including but limited to: taxanes such as docetaxel (TAXITERE), paclitaxel (ABRAXANE, TAXOL), vinca alkaloids such as vincristine (ONCOVIN), vinblastine, vindesine, and vinorelbine (NAVELBINE);
8) topoisomerase inhibitors, including, but not limited to: amacrine, camptothecin (CTP), genistein, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VUMON), mitoxantrone (NOVANTRONE), and etoposide (EPOSIN);
9) DNA replication inhibitors, including, but not limited to: fludarabine (FLUDARA), aphidicolin, ganciclovir, and cidofovir;
10) ribonucleoside diphosphate reductase inhibitors, including, but not limited to: hydroxyurea;
11) transcription inhibitors, including, but not limited to: actinomycin D (dactinomycin, COSMEGEN) and plicamycin (mithramycin);
12) DNA cleaving agents, including, but not limited to: bleomycin (BLENOXANE), idarubicin,
13) cytotoxic antibiotics, including, but not limited to: actinomycin D (dactinomycin, COSMEGEN),
14) aromatase inhibitors, including, but not limited to: aminoglutethimide, anastrozole (ARIMIDEX), letrozole (FEMARA), vorozole (RIVIZOR), and exemestane (AROMASIN);
15) angiogenesis inhibitors, including, but not limited to: genistein, sunitinib (SUTENT), and bevacizumab (AVASTIN);
16) anti-steroids and anti-androgens, including, but not limited to: aminoglutethimide (CYTADREN), bicalutamide (CASODEX), cyproterone, flutamide (EULEXIN), nilutamide(NILANDRON);
17) tyrosine kinase inhibitors, including, but not limited to: imatinib (GLEEVEC), erlotinib (TARCEVA), lapatininb (TYKERB), sorafenib (NEXAVAR), and axitinib (INLYTA);
18) mTOR inhibitors, including, but not limited to: everolimus, temsirolimus (TORISEL), and sirolimus;
19) monoclonal antibodies, including, but not limited to: trastuzumab (HERCEPTIN) and rituximab (RITUXAN);
20) apoptosis inducers such as cordycepin;
21) protein synthesis inhibitors, including, but not limited to: clindamycin, chloramphenicol, streptomycin, anisomycin, and cycloheximide;
22) antidiabetics, including, but not limited to: metformin and phenformin;
23) antibiotics, including, but not limited to:
  a. tetracyclines, including, but not limited to: doxycycline;
  b. erythromycins, including, but not limited to: azithromycin;
  c. glycylglycines, including, but not limited to: tigecycline;
  d. antiphrastic, including, but not limited to: pyrvinium pamoate;
  e. beta-lactams, including, but not limited to the penicillins and cephalosporins;
  f. anthracycline antibiotics, including, but not limited to: daunorubicin and doxorubicin;
  g. other antibiotics, including, but not limited to: chloramphenicol, mitomycin C, and actinomycin;
24) antibody therapeutic agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and
25) other agents, such as *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone;

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating ATR kinase-mediated disorders in a human or animal subject in need of such treatment comprising administering to the subject an amount of a compound disclosed herein effective to reduce or prevent the disorder in the subject, in combination with at least one additional agent for treating the disorder that is known in the art. In a related aspect, certain embodiments provide therapeutic compositions comprising at least one compound disclosed herein in combination with one or more additional agents for treating ATR kinase-mediated disorders.

Specific diseases to be treated by the compounds, compositions, and methods disclosed herein include proliferative and hyperproliferative diseases, including cancer.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

List of Abbreviations

Boc=tert-butyloxycarbonyl; BPin=4,4,5,5-tetramethyl-1,3,2-dioxaborolan-2-yl; $Br_2$=bromine; Bu=n-butyl; t-Bu=tert-butyl=2,2-dimethylethyl; °C.=Celsius; CBz=carboxybenzyl; $CDCl_3$=deuterated chloroform; $CD_3CN$=deuterated acetonitrile; DBN=1,5-Diazabicyclo(4.3.0)non-5-ene; DBU=1,8-diazabicyclo(5.4.0)undec-7-ene; DCM=$CH_2Cl_2$=dichloromethane; DDTT=3-((dimethylaminomethylidene)amino)-3H-1,2,4-dithiazole-5-thione; DIPEA=$iPr_2NEt$=diisopropylethylamine; DMAP=4-Dimethylaminopyridine; DMF=dimethylformamide; DMF-$d_7$=dimethylformamide-$d_7$; DMSO=dimethyl sulfoxide; DMSO-$d_6$=dimethyl sulfoxide-$d_6$; DMTr=dimethoxytrityl=(4-methoxyphenyl)$_2$(phenyl)methyl; $D_2O$=deuterated water; dppf=1,1'-bis(diphenylphosphino)ferrocene; EA=EtOAc=ethyl acetate; ES+=electrospray positive ionization; ES−=electrospray negative ionization; Et=ethyl; EtOH=ethanol; h=hour; H=hydrogen; HCl=hydrogen chloride; $HCO_2NH_4$=ammonium formate; $H_2O$=water; HPLC=high pressure liquid chromatography, also known as preparative high performance liquid chromatography;

int.=intermediate; iPr=isopropyl=2-propyl; M=molar; mCPBA=m-chloroperbenzoic acid; MeCN=CH$_3$CN=acetonitrile; MeOH=methanol; MHz=megahertz; mL=milliliter; min=minute; MS=mass spectrometry; MsCl=methanesulfonyl chloride; MW=microwave; N$_2$=nitrogen; NH$_3$=ammonia; NH$_4$OH=ammonium hydroxide; NMP=N-Methyl-2-pyrrolidone; $^1$H-NMR=proton nuclear magnetic resonance; $^{31}$P-NMR=phosphorous nuclear magnetic resonance; PBS=phosphate buffered saline; PE=petroleum ether; Pin=pinacol=2,3-dimethylbutane-2,3-diol; Pin$_2$B$_2$=4,4,4',4', 5,5,5',5'-octamethyl-2,2'-bi(1,3,2-dioxaborolane); Piv=pivaloyl=(CH$_3$)$_3$C—C(=O)—; prep-HPLC=preparative high pressure liquid chromatography, also known as preparative high performance liquid chromatography; RT=room temperature; NaOH=sodium hydroxide; Pd(dppf)Cl$_2$=[1,1'-bis(diphenylphosphino)ferrocene]palladium(II) dichloride; RuPhos=dicyclohexyl(2',6'-diisopropoxy-[1,1'-biphenyl]-2-yl)phosphine; THF=tetrahydrofuran; Py=pyridine; SFC=supercritical fluid chromatography; TBSCl=tert-butyldimethylsilyl chloride; TEA=triethylamine; TEAB=tetraethyl ammonium bicarbonate; TMSCl=trimethylsilyl chloride; TFA=trifluoroacetic acid; K$_2$CO$_3$=potassium carbonate; μL=μl=microliter.

General Synthetic Methods for Preparing Compounds

The following schemes can be used to practice the present disclosure.

Scheme 1 depicts a Buchwald coupling reaction with dichloropyridine 1 and a sulfoximine, followed by a Suzuki coupling reaction with chloropyridine 2 and a boronic ester affords the pyridine compound 3.

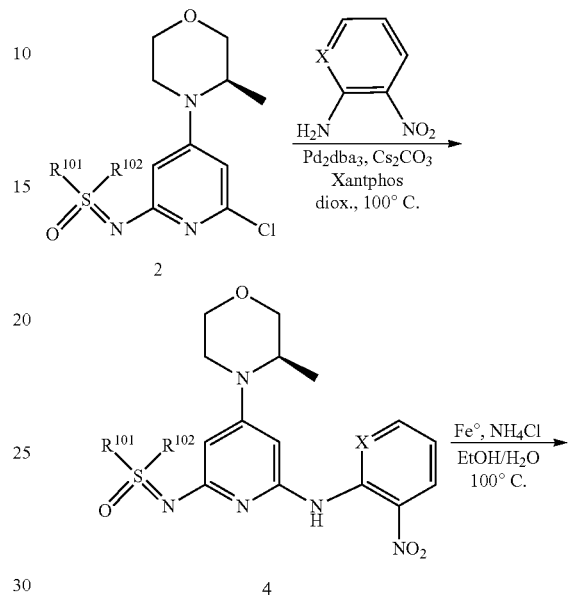

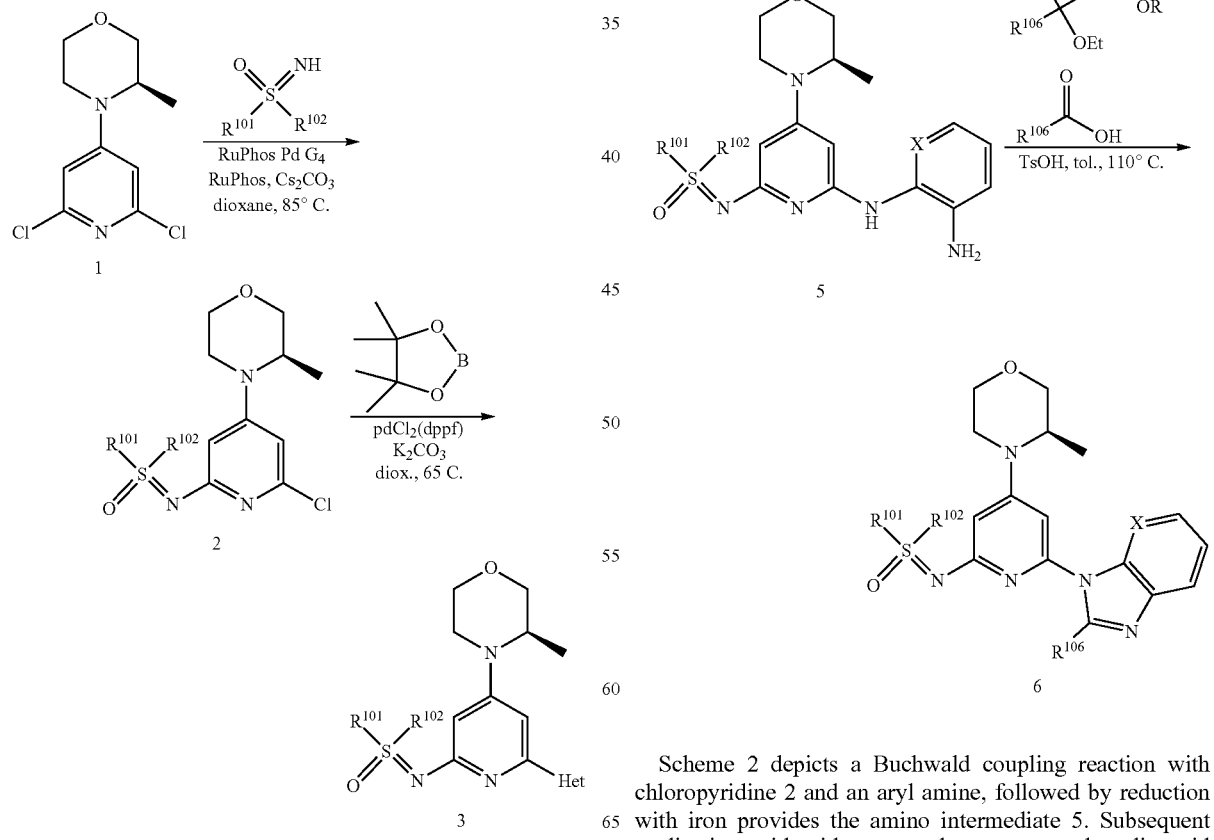

Scheme 2 depicts a Buchwald coupling reaction with chloropyridine 2 and an aryl amine, followed by reduction with iron provides the amino intermediate 5. Subsequent cyclization with either an orthoester or carboxylic acid affords the pyridine compound 6.

Scheme 3

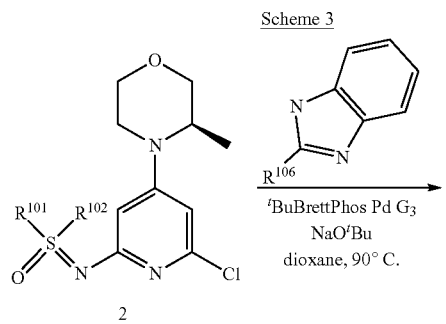

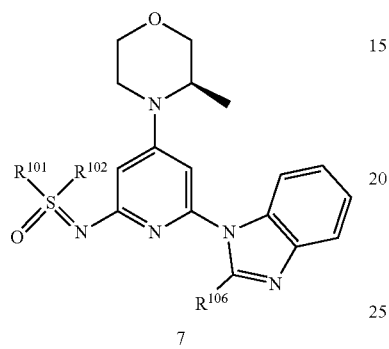

Scheme 3 depicts a Buchwald coupling with chloropyridine 2 and a benzimidazole affords the pyridine compound 6.

General Methods.

The following example compounds are prepared by the methods of Schemes 1-3:

Intermediate A

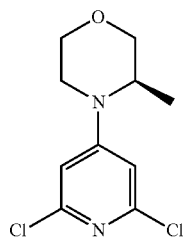

(R)-4-(2,6-Dichloropyridin-4-yl)-3-methylmorpholine

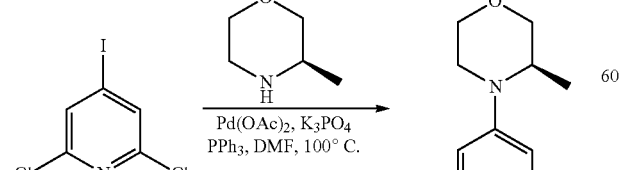

(R)-4-(2,6-Dichloropyridin-4-yl)-3-methylmorpholine

To a solution of 2,6-dichloro-4-iodopyridine (25 g, 93 mmol), PPh$_3$ (2.87 g, 91.6 mmol), Pd(OAc)$_2$ (1.04 g, 4.49 mmol) and K$_3$PO$_4$ (60.2 g, 273.8 mmol) in DMF (400 mL) was added (R)-3-methylmorpholine (17.4 g, 146 mmol) and the reaction mixture was stirred at 100° C. for 4 h. The mixture was cooled to RT and concentrated under reduced pressure. The residue was taken up in EtOAc (200 mL), partitioned with H$_2$O (150 mL) and the layers were separated. The aqueous layer was extracted with EtOAc (3×150 mL). The combined organic layers were washed with water (3×100 mL), dried over Na$_2$SO$_4$, filtered and concentrated under reduced pressure. The residue was purified via flash chromatography (0-10% EtOAc in Hexane) to afford the title compound (17.5 g, 72% yield) as a white solid. MS (ES+) C$_{10}$H$_{12}$Cl$_2$N$_2$O requires: 246, found: 247 [M+H]$^+$.

Intermediate B

Iminodimethyl-λ$^6$-sulfanone

Step 1

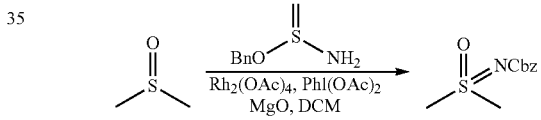

Benzyl (dimethyl(oxo)-λ$^6$-sulfaneylidene)carbamate

To a suspension of DMSO (780 mg, 10.0 mmol), benzyl carbamate (2.3 g, 15 mmol), Rh$_2$(OAc)$_4$ (110 mg, 0.25 mmol) and MgO (1.6 g, 40 mmol) in DCM (100 mL) was added PhI(OAc)$_2$ (4.8 g, 15 mmol). The resulting mixture was stirred at room temperature for 16 h. The reaction mixture was filtered and concentrated under reduced pressure. The residue was purified via flash chromatography (0-90% EtOAc in petroleum ether) to afford the title compound (900 mg, 40% yield) as a white solid. MS (ES+) C$_{10}$H$_{13}$NO$_3$S requires: 227, found: 228 [M+H]$^+$.

Step 2

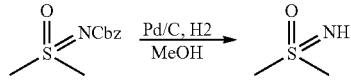

Iminodimethyl-λ$^6$-sulfanone

The product from the previous step (600 mg, 2.6 mmol) and Pd/C (243 mg, 2.6 mmol) were suspended in MeOH (20 mL). The mixture was stirred under an atmosphere of H$_2$ at 1 atm for 16 h. The reaction mixture was purged with N$_2$, filtered through CELITE® and the filtrate was washed with MeOH (10 mL). The mixture was concentrated under reduced pressure to afford the title compound (205 mg, 85% yield) as a colorless oil. MS (ES⁺) C₂H₇NOS requires: 93, found 94 [M+H]⁺.

Intermediate C

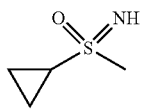

Cyclopropyl(imino)(methyl)-λ⁶-sulfanone

Step 1

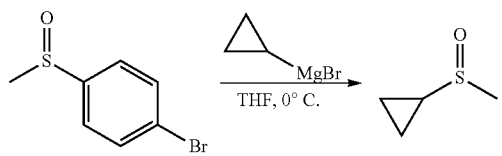

(Methylsulfinyl)cyclopropane:

To a solution of the 1-bromo-4-(methylsulfinyl)benzene (10.5 g, 48.0 mmol) in THF (100 mL) was added cycloproylmagnesium bromide (1M, 72 mL, 72 mmol) at 0° C. slowly. The mixture was stirred at 0° C. for 1.5 h. Saturated aqueous NH₄Cl was added (200 mL), the layers were separated and the aqueous layer was extracted with CH₂Cl₂ (5×150 mL). The combined organic layers were dried over Na₂SO₄, filtered and concentrated under reduced pressure. The residue was purified via flash chromatography (50-100% EtOAc in petroleum ether) to afford the title compound (3.2 g, 64% yield) as a yellow oil. MS (ES⁺) C₄H₈OS requires: 104, found 105 [M+H]⁺.

Step 2

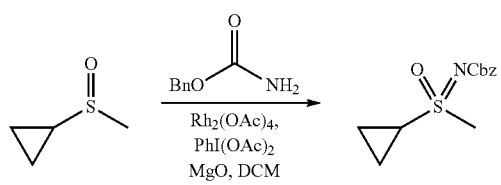

Benzyl (cyclopropyl(methyl)(oxo)-λ⁶-sulfaneylidene)carbamate

To a solution of the product from the previous step (2.35 g, 22.6 mmol) in DCM (100 mL) were added benzyl carbamate (5.1 g, 34 mmol), PhI(OAc)₂ (11 g, 34 mmol), Rh₂(OAc)₄ (0.25 g, 0.56 mmol) and MgO (3.6 g, 90 mmol) and the resulting mixture was stirred at RT for 16 h. The reaction mixture was filtered through CELITE® and concentrated under reduced pressure. The residue was purified via flash chromatography (20-50% EtOAc in petroleum ether) to afford the title compound (2.2 g, 39% yield) as a yellow oil. MS (ES⁺) C₁₂H₁₅NO₃S requires: 253, found 254 [M+H]⁺.

Step 3

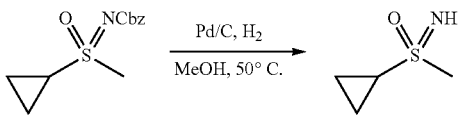

Cyclopropyl(imino)(methyl)-λ⁶-sulfanone

To a solution of the product from the previous step (2.2 g, 8.7 mmol) in MeOH (100 mL) was added Pd/C (2.2 g) under N₂. The N₂ atmosphere was evacuated and purged with H₂ (3×). The mixture was heated to 50° C. and stirred for 3 h under a H₂ atmosphere. The mixture was cooled to RT, filtered through CELITE® and concentrated under reduced pressure to afford the title compound (1.05 g, 96% yield) as a yellow oil. MS (ES⁺) C₄H₉NOS requires: 119, found 120 [M+H]⁺.

Intermediate D

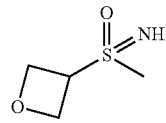

Imino(methyl)(oxetan-3-yl)-λ⁶-sulfanone

Step 1

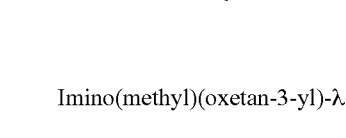

3-(Methylsulfinyl)oxetane

To a solution of 3-iodooxetane (6.0 g, 32.6 mmol) in DMF (60 mL) was added CH₃SNa (2.28 g, 32.6 mmol) under N₂. The reaction mixture was stirred at room temperature for 1 h. EtOAc (120 mL) and water (80 mL) were added, the layers were separated and the organic layer was washed with brine (80 mL), dried over MgSO₄ and filtered. The solution of EtOAc was added MeOH (60 mL), water (60 mL) and NaIO₄ (6.2 g, 29.3 mmol) and the reaction mixture was stirred at room temperature for 16 h. The mixture was filtered and concentrated under reduced pressure. The residue was purified via flash chromatography (50% EtOAc in petroleum ether to 10% MeOH in DCM) to afford the title compound (3.5 g, 90% yield) as pale-yellow oil. MS (ES⁺) C₄H₈O₂S requires: 120, found 121 [M+H]⁺.

Step 2

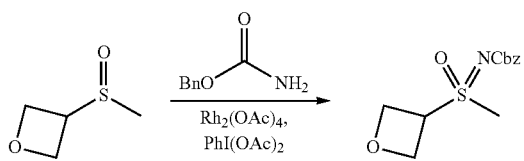

Benzyl (methyl(oxetan-3-yl)(oxo)-λ⁶-sulfaneylidene)carbamate

To a solution of the product from the previous step (3.5 g, 29 mmol) in DCM (260 mL) were added benzyl carbamate (6.58 g, 43.6 mmol), Rh$_2$(OAc)$_4$ (383 mg, 0.873 mmol), PhI(OAc)$_2$ (14.0 g, 43.6 mmol) and MgO (4.7 g, 116 mmol) and the mixture was stirred at room temperature under an atmosphere of N$_2$ for 16 h. The reaction mixture was filtered through CELITE® and concentrated under reduced pressure. The residue was purified via flash chromatography (20-50% EtOAc in petroleum ether) to afford the title compound (4.1 g, 52% yield) as pale-yellow oil. MS (ES$^+$) C$_{12}$H$_{15}$NO$_4$S requires: 269, found 270 [M+H]$^+$.

Step 3

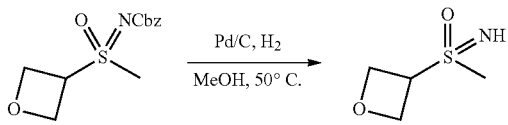

Imino(methyl)(oxetan-3-yl)-λ⁶-sulfanone

To a solution of the product from the previous step (4.1 g, 15 mmol) in MeOH (60 mL) was added Pd/C (4.1 g) under N$_2$. The atmosphere was removed and purged three times with H$_2$. The mixture was heated to 50° C. and stirred for 3 h under a H$_2$ atmosphere. The mixture was cooled to room temperature, filtered through CELITE®, and concentrated under reduced pressure to afford the title compound (1.7 g, 83% yield) as pale-yellow oil.

MS (ES$^+$) C$_4$H$_9$NO$_2$S requires: 135, found 136 [M+H]$^+$.

Intermediate E

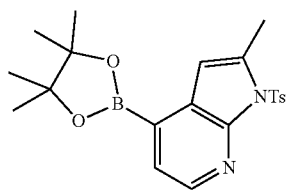

2-Methyl-4-(4,4,5,5-tetramethyl-1,3,2-dioxaborolan-2-yl)-1-tosyl-1H-pyrrolo[2,3-b]pyridine Step 1

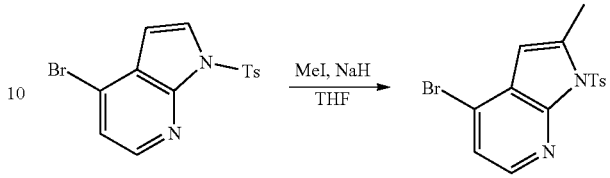

4-Bromo-2-methyl-1-tosyl-1H-pyrrolo[2,3-b]pyridine

To a solution of 4-bromo-1-tosyl-1H-pyrrolo[2,3-b]pyridine (1.0 g, 2.9 mmol) in THF (30 mL) at −78° C. was added LDA (2.9 mL, 2 M, in THF) and the mixture was stirred for 1 h at −78° C. under an atmosphere of Ar. MeI (4.0 g, 29 mmol) was added and the mixture was allowed to warm to room temperature and stirred for 3 h. Saturated aqueous NH$_4$Cl (50 mL) was added and the aqueous layer was extracted with EtOAc (3×50 mL). The combined organic layers were dried over Na$_2$SO$_4$, filtered and concentrated under reduced pressure. The residue was purified by reverse phase preparative HPLC (Mobile phase: A=10 mM NH$_4$HCO$_3$/H$_2$O, B=MeCN; Gradient: B=65-95%; 18 min; Column: Welch XB-C18, 10 μm, 21.2×250 mm) to afford the title compound (420 mg, 40% yield) as a white solid. MS (ES$^+$) C$_{15}$H$_{13}$BrN$_2$O$_2$S requires: 364, found 365 [M+H]$^+$.

Step 2

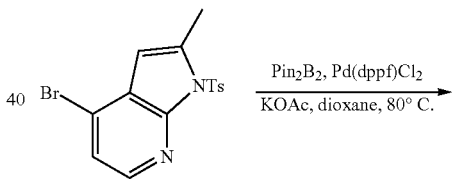

2-Methyl-4-(4,4,5,5-tetramethyl-1,3,2-dioxaborolan-2-yl)-1-tosyl-1H-pyrrolo[2,3-b]pyridine A reaction vial was charged with the product from the previous reaction (410 mg, 1.13 mmol), 4,4,4',4',5,5,5',5'-octamethyl-2,2'-bi(1,3,2-dioxaborolane) (345 mg, 1.3 mmol), KOAc (277 mg, 2.8 mmol) and Pd(dppf)Cl$_2$ (82 mg, 0.11 mmol) in dioxane (5 mL). The mixture was degassed by bubbling Ar for 1 min. The mixture was heated at 80° C. and stirred for 5 hrs. The mixture was cooled to room temperature, filtered through CELITE®, and concentrated under reduced pressure. the residue was purified via flash chromatography (20% EtOAc in petroleum ether) to afford the title compound (350 mg, 75% yield) as a white solid. MS (ES$^+$) C$_{21}$H$_{25}$BN$_2$O$_4$S requires 412, found 331 [M−81]$^+$

Intermediate F

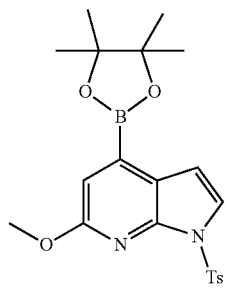 [SMILES: COc1cc(B2OC(C)(C)C(C)(C)O2)c2ccn(S(=O)(=O)c3ccc(C)cc3)c2n1]

6-Methoxy-4-(4,4,5,5-tetramethyl-1,3,2-dioxaborolan-2-yl)-1-tosyl-1H-pyrrolo[2,3-b]pyridine Step 1

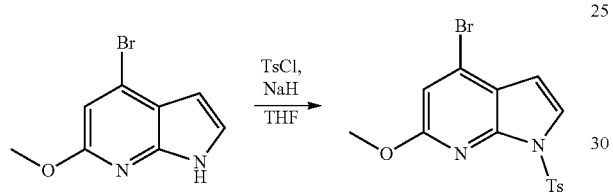

4-Bromo-6-methoxy-1-tosyl-1H-pyrrolo[2,3-b]pyridine

To a solution of 4-bromo-6-methoxy-1H-pyrrolo[2,3-b]pyridine (800 mg, 3.5 mmol) in THF (50 mL) at 0° C. under an atmosphere of $N_2$ was added sodium hydride (60 percent in mineral oil, 280 mg, 7.0 mmol) slowly. The reaction mixture could warm to room temperature and stirred for 30 min. 4-methylbenzene-1-sulfonyl chloride (798 mg, 4.2 mmol) was added and the reaction mixture was stirred at RT for 2 hours. Water was added (1 mL) and the mixture was concentrated under reduced pressure. The residue was dissolved in DCM (100 mL), washed with 2 M sodium carbonate (2×30 mL), dried over $MgSO_4$, filtered and concentrated under reduced pressure. The residue was purified via flash chromatography (0-50% EtOAc in hexanes) to afford the title compound (1.2 g, 90% yield) as a white solid. MS (ES$^+$) $C_{15}H_{13}BrN_2O_3S$ requires 380, found 381[M+H]$^+$.

Step 2

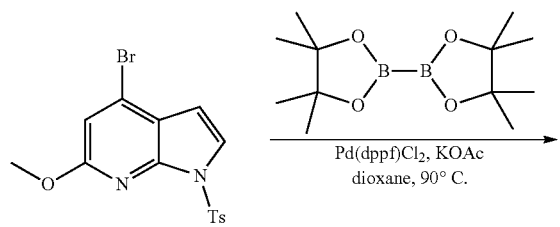

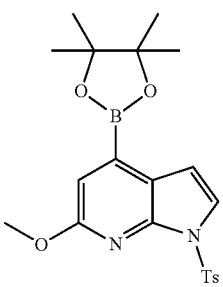

6-Methoxy-4-(4,4,5,5-tetramethyl-1,3,2-dioxaborolan-2-yl)-1-tosyl-1H-pyrrolo[2,3-b]pyridine A reaction vial was charged with the product from the previous reaction (500 mg, 1.3 mmol), 4,4,4',4',5,5,5',5'-octamethyl-2,2'-bi(1,3,2-dioxaborolane) (498 mg, 1.97 mmol), Pd(dppf)Cl$_2$ (95 mg, 0.13 mmol) and KOAc (382 mg, 3.9 mmol) in dioxane (5 mL). The mixture was degassed by bubbling Ar for 1 min. The mixture was heated at 90° C. and stirred for 16 h. The mixture was cooled to room temperature, filtered through CELITE®, and concentrated under reduced pressure. the residue was purified via flash chromatography (0-25% EtOAc in hexanes) to afford the title compound (350 mg, 75% yield) as a white solid. MS (ES$^+$) $C_{21}H_{25}BN_2O_5S$ requires 428, found 347 [M−81]$^+$.

Intermediate G

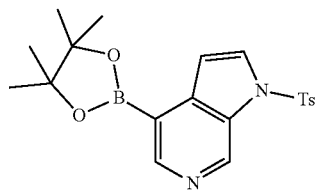 [SMILES: Cc1ccc(S(=O)(=O)n2ccc3c(B4OC(C)(C)C(C)(C)O4)cncc32)cc1]

4-(4,4,5,5-Tetramethyl-1,3,2-dioxaborolan-2-yl)-1-tosyl-1H-pyrrolo[2,3-c]pyridine

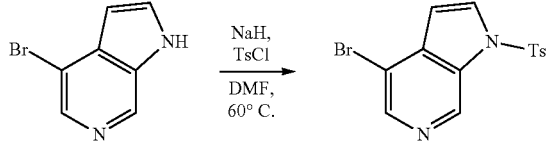 [SMILES: Brc1cncc2[nH]ccc12 ; Cc1ccc(S(=O)(=O)n2ccc3c(Br)cncc32)cc1]

4-Bromo-1-tosyl-1H-pyrrolo[2,3-c]pyridine

To a solution of 4-bromo-1H-pyrrolo[2,3-c]pyridine (300 mg, 1.5 mmol) in DMF (10 mL) at 0° C. was added NaH (92 mg, 2.25 mmol, 60%) and the reaction mixture was stirred at 0° C. for 2 h. The reaction mixture was allowed to warm to room temperature, TsCl (429 mg, 2.25 mmol) was added and the mixture was heated to 60° C. and stirred for an additional 2 h. H$_2$O (10 mL) was added, the layers were separated and the aqueous layer was extracted with EtOAc (3×15 mL). The combined organic layers were dried over Na$_2$SO$_4$, filtered and concentrated under reduced pressure. The residue was purified by flash chromatography (0-20% EtOAc in petroleum ether) to afford the title compound (300 mg, 57% yield) as a white solid. MS (ES$^+$) C$_{14}$H$_{11}$BrN$_2$O$_2$S requires 350, found 351 [M−81]$^+$.

Step 2

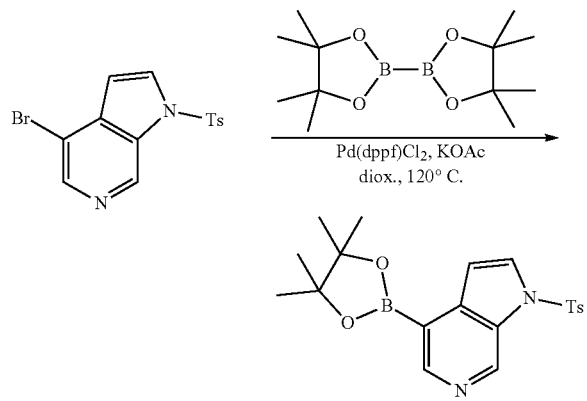

4-(4,4,5,5-Tetramethyl-1,3,2-dioxaborolan-2-yl)-1-tosyl-1H-pyrrolo[2,3-c]pyridine A mixture of the product from the previous step (300 mg, 0.86 mmol), 4,4,4',4',5,5,5',5'-octamethyl-2,2'-bi(1,3,2-dioxaborolane) (254 mg, 1.0 mmol), Pd(dppf)Cl$_2$ (63 mg, 0.086 mmol) and KOAc (169 mg, 1.72 mmol) in dioxane (10 mL) was degassed with Ar and the reaction mixture was heated at 120° C. for 4 h. The reaction mixture was cooled to room temperature, filtered through CELITE®, and concentrated under reduced pressure. The residue was purified by flash chromatography (10-60% EtOAc in petroleum ether) to afford the title compound (100 mg, 29% yield) as a white solid. MS (ES$^+$) C$_{20}$H$_{23}$BN$_2$O$_4$S requires 398, found 399 [M+H]$^+$.

Intermediate H

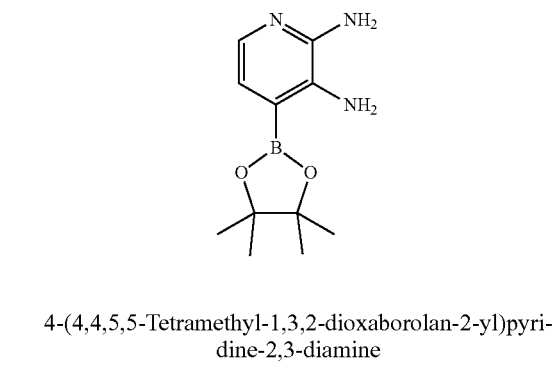

4-(4,4,5,5-Tetramethyl-1,3,2-dioxaborolan-2-yl)pyridine-2,3-diamine

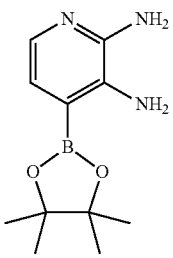

4-(4,4,5,5-Tetramethyl-1,3,2-dioxaborolan-2-yl)pyridine-2,3-diamine: To a solution of 4-bromopyridine-2,3-diamine (200 mg, 1.07 mmol), KOAc (262 mg, 2.67 mmol) and 4,4,4',4',5,5,5',5'-octamethyl-2,2'-bi(1,3,2-dioxaborolane) (544 mg, 2.14 mmol) in dioxane (10 mL) was added Pd(dppf)Cl$_2$ (63 mg, 0.086 mmol) and the mixture was stirred at 80° C. for 16 h under an atmosphere of Ar. The reaction mixture was cooled to RT, filtered through CELITE®, and concentrated under reduced pressure. The residue was taken up in petroleum ether (20 mL) and stirred for 10 minutes, filtered, and concentrated to afford the title compound (>250 mg, assumed quantitative) as a brown solid. (ES$^+$) C$_{11}$H$_{18}$BN$_3$O$_2$ requires: 235, found 154 [M−81]$^+$.

Intermediate I

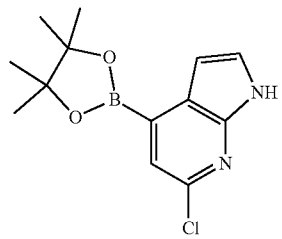 [SMILES: CC1(C)OB(c2cc(Cl)nc3[nH]ccc23)OC1(C)C]

6-Chloro-4-(4,4,5,5-tetramethyl-1,3,2-dioxaborolan-2-yl)-1H-pyrrolo[2,3-b]pyridine

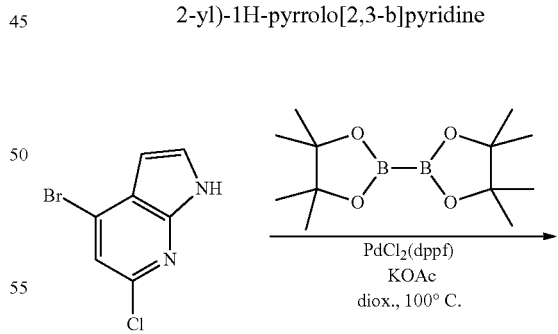

6-Chloro-4-(4,4,5,5-tetramethyl-1,3,2-dioxaborolan-2-yl)-1H-pyrrolo[2,3-b]pyridine A suspension of 4-bromo-6-chloro-1H-pyrrolo[2,3-b]pyridine (100 mg, 0.432 mmol), 4,4,4',4',5,5,5',5'-octamethyl-2,2'-bi(1,3,2-dioxaborolane) (121 mg, 0.475 mmol) and potassium acetate (127 mg, 1.30 mmol) in dioxane (2160 μL) was degassed with N₂ for 1 minute. PdCl₂(dppf)-CH₂Cl₂ (17 mg, 0.022 mmol) was added and the mixture was degassed with N₂ for an additional 1 minute. The reaction mixture was heated to 100° C. and stirred for 12 h. The mixture was cooled to room temperature, filtered through CELITE® and concentrated under reduced pressure to afford the title compound (assumed quantitative) as a brown solid. MS (ES+) $C_{13}H_{16}BClN_2O_2$ requires: 278, found: 279 [M+H]⁺.

Intermediate J

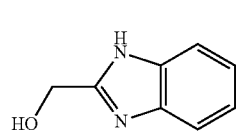

2-(((Triisopropylsilyl)oxy)methyl)-1H-benzo[d]imidazole

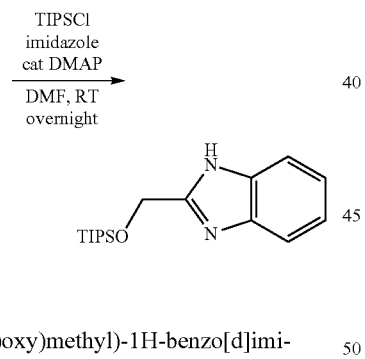

2-(((Triisopropylsilyl)oxy)methyl)-1H-benzo[d]imidazole

To a solution of (1H-benzo[d]imidazol-2-yl)methanol (1.66 g, 11.2 mmol), imidazole (0.92 g, 13.4 mmol) and DMAP (68 mg, 0.56 mmol) in DMF (10 mL) at room temperature was added chlorotriisopropylsilane (2.87 mL, 13.5 mmol) and the reaction mixture was stirred at room temperature for 16 h. The mixture was poured into water (100 mL), the layers were separated and the aqueous layer was extracted with diethyl ether (2×100 mL). The combined organic layers were washed with water (2×50 mL) and brine (50 mL), dried over MgSO₄, filtered and concentrated under reduced pressure to afford the title compound (3.40 g, 100% yield) as a white solid. MS (ES⁺) $C_{17}H_{28}N_2OSi$ requires: 304, found: 305 [M+H]⁺.

Example 1

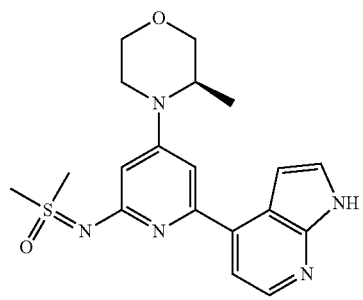 [SMILES: C[C@@H]1COCCN1c1cc(N=S(C)(C)=O)nc(-c2ccnc3[nH]ccc23)c1]

(R)-Dimethyl((4-(3-methylmorpholino)-6-(1H-pyrrolo[2,3-b]pyridin-4-yl)pyridin-2-yl)imino)-λ⁶-sulfanone

Step 1

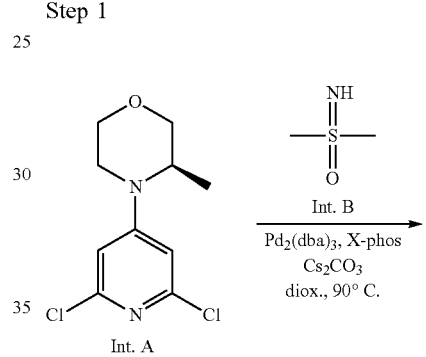

(R)-((6-Chloro-4-(3-methylmorpholino)pyridin-2-yl)imino)dimethyl-λ⁶-sulfanone

A mixture of Int. A (5.0 g, 20 mmol), Int. B (1.86 g, 20 mmol), Pd₂(dba)₃ (900 mg, 0.1 mmol), X-phos (480 mg, 0.10 mmol) and Cs₂CO₃ (13 g, 40 mmol) in dioxane (100 mL) was heated to 90° C. for 16 h. The reaction mixture was cooled to RT, filtered through CELITE®® and concentration under reduced pressure. The residue was purified via flash chromatography (10-75% EtOAc in petroleum ether) to afford the title compound (3.4 g, 56% yield) as a white solid. MS (ES⁺) $Cl_2H_{18}C_1N_3O_2S$ requires: 303, found 304 [M+H]⁺.

Step 2

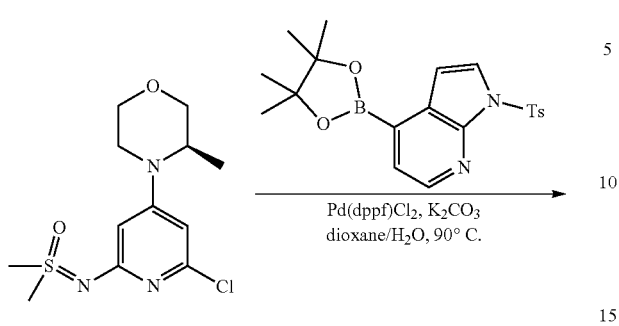 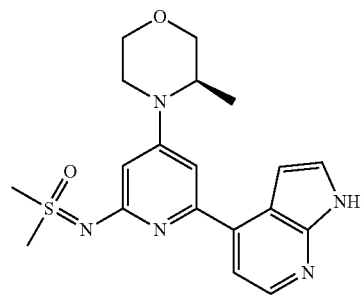

Pd(dppf)Cl₂, K₂CO₃
dioxane/H₂O, 90° C.

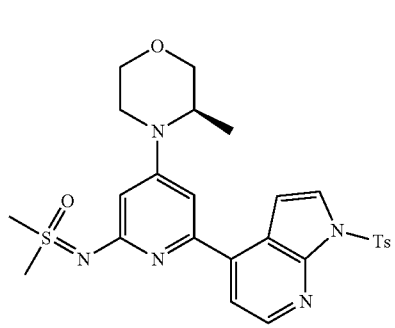

(R)-Dimethyl((4-(3-methylmorpholino)-6-(1-tosyl-1H-pyrrolo[2,3-b]pyridin-4-yl)pyridin-2-yl)imino)-λ⁶-sulfanone Under Ar atmosphere, a mixture of the product from the previous step (4.5 g, 14.85 mmol), 4-(4,4,5,5-tetramethyl-1,3,2-dioxaborolan-2-yl)-1-tosyl-H-pyrrolo[2,3-b]pyridine (7.1 g, 17.82 mmol), Pd(dppf)Cl₂ (1.09 g, 1.49 mmol) and K₂CO₃ (6.2 g, 44.6 mmol) in dioxane/H₂O (120 mL/24 mL) was heated to 90° C. for 16 h. The mixture was cooled to room temperature, filtered through CELITE® and concentration under reduced pressure. The residue was purified by flash chromatography (10-80% EtOAc in petroleum ether) to afford the title compound (6.48 g, 81% yield) as a brown solid. MS (ES⁺) C₂₆H₂₉N₅O₄S₂ requires: 539, found: 540 [M+H]⁺.

Step 3

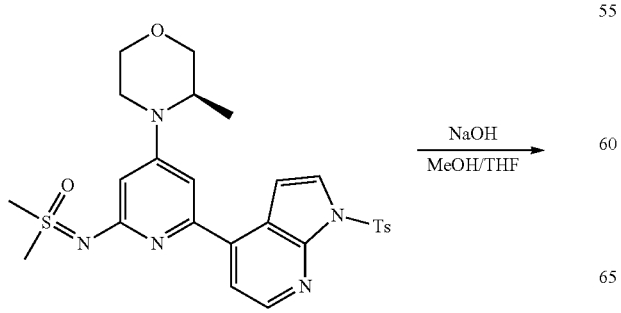

NaOH
MeOH/THF

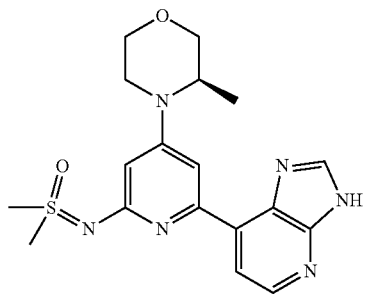 [SMILES: C[C@@H]1COCCN1c1cc(N=S(C)(C)=O)nc(-c2ccnc3[nH]cnc23)c1]

(R)-Dimethyl((4-(3-methylmorpholino)-6-(1H-pyrrolo[2,3-b]pyridin-4-yl)pyridin-2-yl)imino)-λ⁶-sulfanone To a solution of the product from the previous step (10 g, 18.55 mmol) in MeOH (150 mL) and THF (75 mL) was added aqueous NaOH (5 N, 37 mL, 186 mmol). The reaction mixture was at 50° C. and stirred for 2 h. The mixture was cooled to room temperature, 2N HCl was added until a pH between 6 and 7 was obtained, water (200 mL) was added and the aqueous layer was extracted with DCM (3×200 mL). The combined organic layers were dried over Na₂SO₄, filtered and concentrated under reduced pressure. The residue was purified by flash chromatography (2-5% MeOH in DCM) to afford the title compound (4.9 g, 68% yield) as a yellow solid.

¹H NMR (500 MHz, DMSO-d₆) δ 11.68 (s, 1H), 8.26 (d, J=5.0 Hz, 1H), 7.49 (dd, J=6.7, 4.1 Hz, 2H), 7.81 (dd, J=3.4, 2.0 Hz, 1H), 6.96 (d, J=1.9 Hz, 1H), 6.09 (d, J=1.9 Hz, 1H), 4.06 (d, J=6.8 Hz, 1H), 3.94 (dd, J=10.8, 3.4 Hz, 1H), 3.69 (dt, J=11.4, 7.0 Hz, 2H), 3.52 (dt, J=24.2, 8.0 Hz, 2H), 3.38 (d, J=4.5 Hz, 6H), 3.11-3.01 (m, 1H), 1.12 (d, J=6.6 Hz, 3H) ppm. MS (ES⁺) C₁₉H₂₃N₅O₂S requires: 385, found: 386 [M+H]⁺.

Example 2

(R)-((6-(3H-Imidazo[4,5-b]pyridin-7-yl)-4-(3-methylmorpholino)pyridin-2-yl)imino)dimethyl-λ⁶-sulfanone Step 1

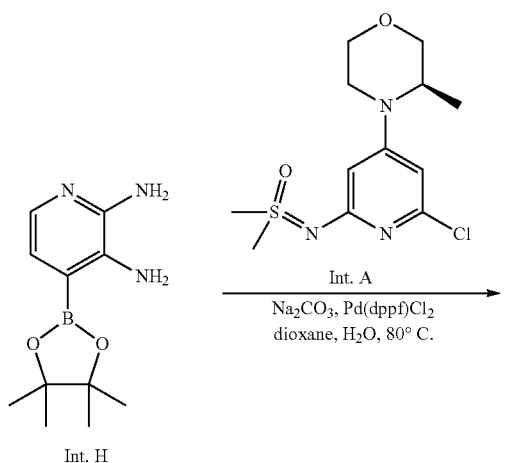

Step 2

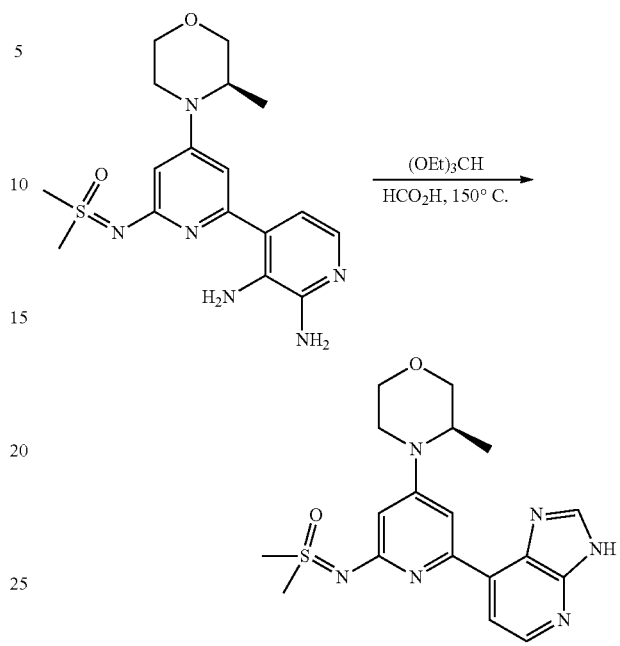

(R)-((6-(3H-Imidazo[4,5-b]pyridin-7-yl)-4-(3-methylmorpholino)pyridin-2-yl)imino)dimethyl-λ⁶-sulfanone A microwave vial was charged with the product from the previous step (130 mg, 0.34 mmol), formic acid (48 mg, 1.0 mmol) and triethyl orthoformate (3 mL) and degassed with Ar for 1 min. The mixture was heated at 150° C. for 1.5 h in a microwave reactor. The mixture was concentrated under reduced pressure. The residue was purified by reverse phase preparative HPLC (Mobile Phase: A=10 mM NH$_4$HCO$_3$/H$_2$O, B=MeCN; Gradient: B=18-48%; 18 min; Column: Welch XB-C18, 10 μm, 21.2×250 mm, 30 mL/min) to afford the title compound (32 mg, 21% yield) as a white solid. $^1$H NMR (500 MHz, DMSO-d$_6$) δ 12.49 (s, 1H), 8.59-8.35 (m, 2H), 7.96 (dd, 1H), 7.29 (s, 1H), 6.11 (d, 1H), 4.17 (d, 1H), 3.97 (t, 1H), 3.82-3.49 (m, 4H), 3.42 (d, 6H), 3.16-3.02 (m, 1H), 1.13 (d, 3H) ppm; MS (ES+) C$_{18}$H$_{22}$N$_6$O$_2$S requires: 386, found: 387 [M+H]$^+$.

(R)-((2',3'-Diamino-4-(3-methylmorpholino)-[2,4'-bipyridin]-6-yl)imino)dimethyl-λ⁶-sulfanone A mixture of Int. A (150 mg, 0.49 mmol), Int. H (350 mg, assumed 1.07 mmol), Na$_2$CO$_3$ (130 mg, 1.2 mmol) and Pd(dppf)Cl$_2$ (18 mg, 0.024 mmol) in dioxane (20 mL) and H$_2$O (4 mL) was heated at 80° C. and stirred for 16 h under an atmosphere of Ar. The reaction mixture was cooled to room temperature, filtered through CELITE® and concentrated under reduced pressure. The residue was purified by flash chromatography (1-15%) MeOH in DCM) to afford the title compound (150 mg, 80% yield) as a brown solid. MS (ES$^+$) C$_{17}$H$_{24}$N$_6$O$_2$S requires: 376, found: 377 [M+H]$^+$.

Example 3a/b

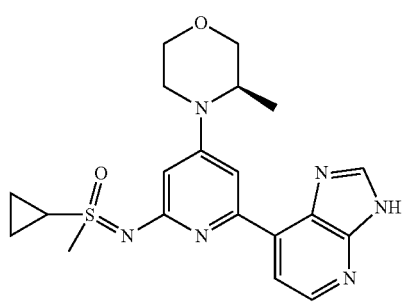 [SMILES: C[C@@H]1COCCN1c1cc(N=S(C)(=O)C2CC2)nc(-c2ccnc3[nH]cnc23)c1]

(R)-Cyclopropyl(methyl)((4-((R)-3-methylmor-
pholino)-6-(1H-pyrrolo[2,3-b]pyridin-4-yl)pyridin-
2-yl)imino)-λ⁶-sulfanone and (S)-cyclopropyl(methyl)((4-((R)-3-methylmor-
pholino)-6-(1H-pyrrolo[2,3-b]pyridin-4-yl)pyridin-
2-yl)imino)-λ⁶-sulfanone

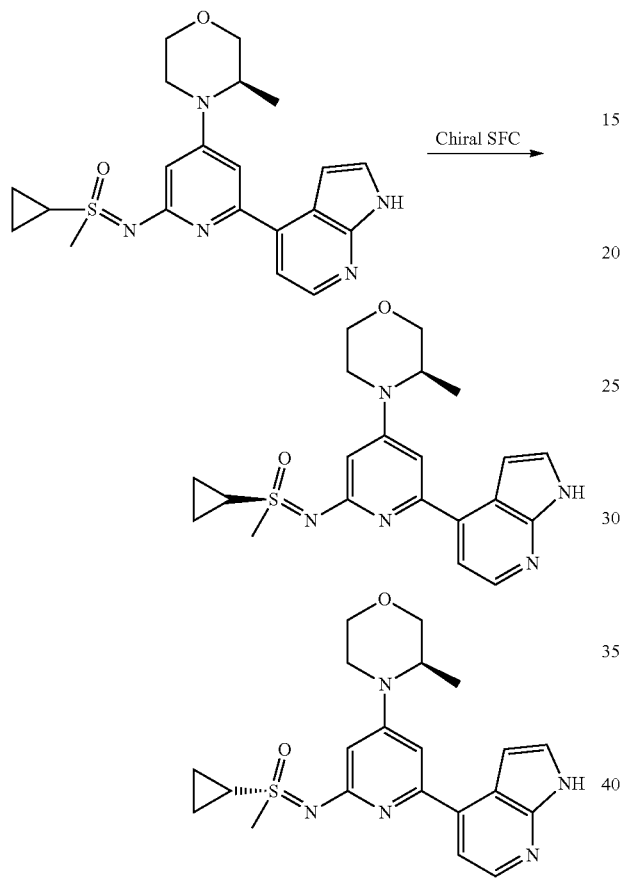

(R)-Cyclopropyl(methyl)((4-((R)-3-methylmorpholino)-6-(1H-pyrrolo[2,3-b]pyridin-4-yl)pyridin-2-yl)imino)-λ⁶-sulfanone and (S)-cyclopropyl(methyl)((4-((R)-3-methylmorpholino)-6-(1H-pyrrolo[2,3-b]pyridin-4-yl)pyridin-2-yl)imino)-λ⁶-sulfanone: Cyclopropyl(methyl)((4-((R)-3-methylmorpholino)-6-(1H-pyrrolo[2,3-b]pyridin-4-yl)pyridin-2-yl)imino)-λ⁶-sulfanone was synthesized according to Example 1. The mixture of compounds was separated chiral SFC (Mobile phase: CO₂/MeOH (0.2% Methanol Ammonia)=40/60; Flow rate: 80 g/min; 3.5 min; Column temperature: 35° C.; Back pressure: 100 bar; Column: Daicel CHIRALPAK® AD, 10 am, 20 mm×250 mm) to afford the title compounds 3a (150 mg, 38% yield, 99% ee) and 3b (148 mg, 37% yield, 96% ee) as white solids. Example CP-AR-0360: R$_f$=1.7 min, Example CP-AR-0361: R$_f$=2.43 min.

Example 3a: ((S)-Cyclopropyl(methyl) or (R)-cyclopropyl(methyl))

R$_f$=1.7 min: ¹H NMR (500 MHz, DMSO-d₆) δ 11.68 (s, 1H), 8.26 (d, J=5.0 Hz, 1H), 7.51-7.46 (m, 2H), 7.16 (dd, J=3.4, 2.0 Hz, 1H), 6.96 (d, J=2.1 Hz, 1H), 6.10 (d, J=2.1 Hz, 1H), 4.11-4.03 (m, 1H), 3.98-3.91 (m, 1H), 3.72 (d, J=11.3 Hz, 1H), 3.67 (dd, J=11.0, 2.8 Hz, 2H), 3.57-3.48 (m, 1H), 3.47 (s, 3H), 3.06 (td, J=12.4, 11.8, 3.6 Hz, 1H), 2.97-2.88 (m, 1H), 1.22-1.14 (m, 2H), 1.13 (d, J=6.6 Hz, 3H), 1.10-0.99 (m, 2H) ppm; MS (ES⁺) C₂₁H₂₅N₅O₂S requires: 411, found: 412 [M+H]⁺.

Example 3b: ((S)-Cyclopropyl(methyl) or (R)-cyclopropyl(methyl))

R$_f$=2.4 min: ¹H NMR (500 MHz, DMSO-d₆) δ 11.67 (s, 1H), 8.26 (d, J=5.0 Hz, 1H), 7.52-7.46 (m, 2H), 7.16 (dd, J=3.5, 1.9 Hz, 1H), 6.96 (d, J=2.2 Hz, 1H), 6.10 (d, J=2.1 Hz, 1H), 4.11-4.04 (m, 1H), 3.94 (dd, J=11.3, 3.7 Hz, 1H), 3.72 (d, J=11.2 Hz, 1H), 3.67 (dd, J=11.3, 3.0 Hz, 1H), 3.54 (dd, J=12.0, 3.1 Hz, 1H), 3.51-3.44 (m, 4H), 3.07 (td, J=12.2, 3.9 Hz, 1H), 2.99-2.90 (m, 1H), 1.22-1.13 (m, 2H), 1.11 (d, J=6.6 Hz, 3H), 1.09-0.98 (m, 2H); MS (ES⁺) C₂₁H₂₅N₅O₂S requires: 411, found: 412 [M+H]⁺.

Example 4

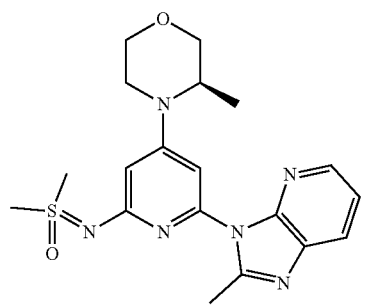 [SMILES: Cc1nc2cccnc2n1-c1cc(N2CCOC[C@H]2C)cc(N=S(C)(C)=O)n1]

(R)-Dimethyl((6-(2-methyl-3H-imidazo[4,5-b]pyridin-3-yl)-4-(3-methylmorpholino)pyridin-2-yl)imino)-λ⁶-sulfanone Step 1

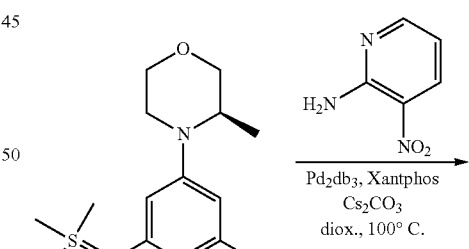

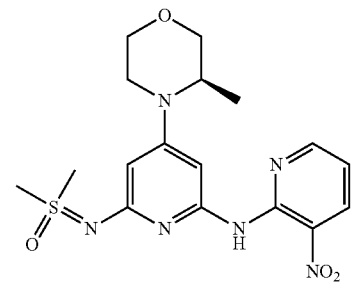

(R)-Dimethyl((4-(3-methylmorpholino)-6-((3-nitropyridin-2-yl)amino)pyridin-2-yl)imino)-λ⁶-sulfanone A reaction vial was charged with (R)-((6-chloro-4-(3-methylmorpholino)pyridin-2-yl)imino)dimethyl-λ⁶-sulfanone (Example 1, step 1) (200 mg, 0.658 mmol), 3-nitropyridin-2-amine (110 mg, 0.790 mmol), and dioxane (3.29 mL) and the mixture was degassed with $N_2$ for 30 seconds. $Cs_2CO_3$ (643 mg, 1.98 mmol), $Pd_2dba_3$ (60 mg, 0.066 mmol) and Xantphos (76 mg, 0.13 mmol) were added and the mixture was degassed with $N_2$ for 30 seconds. The vial was sealed and heated at 100° C. for 16 h. The mixture was cooled to RT, filtered through CELITE®, and concentrated under reduced pressure. The residue was purified via flash chromatography (0-10% MeOH in DCM) to afford the title compound (244 mg, 46% yield) as an orange solid. MS (ES+) $C_{17}H_{22}N_6O_4S$ requires: 406, found: 407 $[M+H]^+$.

Step 2

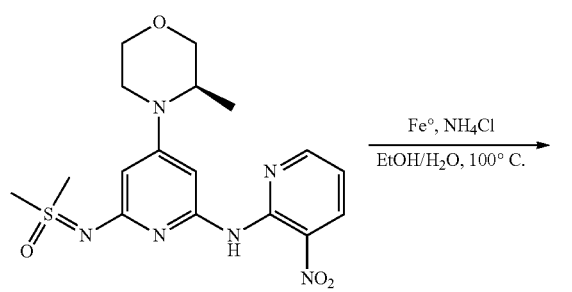

(R)-((6-((3-Aminopyridin-2-yl)amino)-4-(3-methylmorpholino)pyridin-2-yl)imino)dimethyl-λ⁶-sulfanone To a solution of the product from the previous step (244 mg, 0.300 mmol) in EtOH (1.5 mL) were added ammonium chloride (64 mg, 1.2 mmol), water (500 μL), and iron (67 mg, 1.2 mmol) and the resulting mixture was stirred at 100° C. for 3 h. The mixture was cooled to RT, filtered through CELITE® and concentrated under reduced pressure. The residue was purified via flash chromatography (0-20% MeOH in DCM) to afford the title compound (84 mg, 74% yield) as a pale yellow solid. MS (ES+) $C_{17}H_{24}N_6O_2S$ requires: 376, found: 377 $[M+H]^+$.

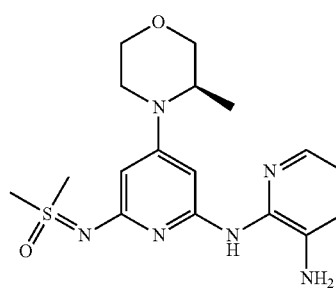

Step 3

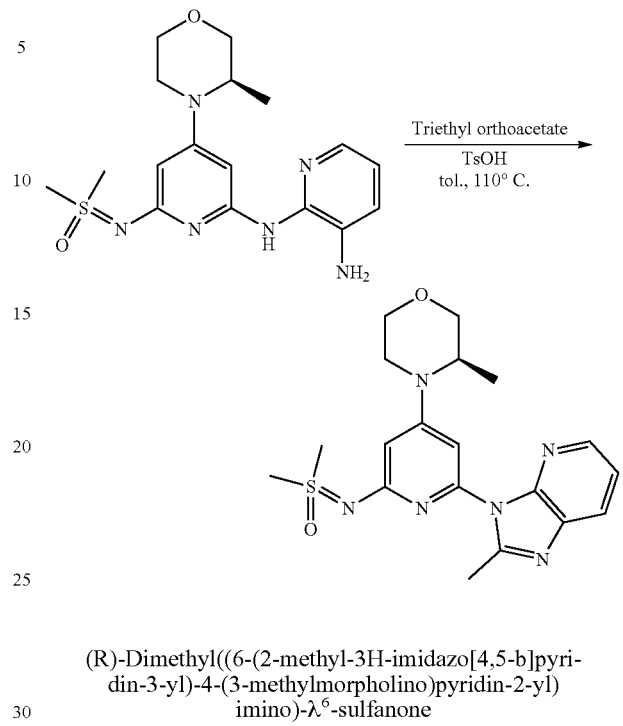

(R)-Dimethyl((6-(2-methyl-3H-imidazo[4,5-b]pyridin-3-yl)-4-(3-methylmorpholino)pyridin-2-yl)imino)-λ⁶-sulfanone To a solution of the product from the previous step (50 mg, 0.13 mmol) in toluene (266 μL) were added triethyl orthoacetate (49 μL, 0.27 mmol) and TsOH (2.5 mg, 0.013 mmol) and the resulting mixture was stirred at 110° C. for 16 h. The mixture was cooled to room temperature and concentrated under reduced pressure. The residue was purified by mass-triggered preparative HPLC (Mobile phase: A=0.1% TFA/$H_2O$, B=0.1% TFA/MeCN; Gradient: B=10-40%; 26 min; Column: XBridge Cis, 5 am, 19 mm×150 mm) to afford the title compound (37 mg, 44% yield) as a white solid.

$^1$H NMR (600 MHz, Methanol-$d_4$) δ 8.39 (d, J=4.9 Hz, 1H), 8.13 (d, J=8.0 Hz, 1H), 7.50-7.44 (m, 1H), 7.04 (s, 1H), 6.54 (s, 1H), 4.15-4.09 (m, 1H), 4.03 (dd, J=11.7, 3.9 Hz, 1H), 3.82 (d, J=11.8 Hz, 1H), 3.77 (d, J=12.0 Hz, 1H), 3.69 (d, J=13.3 Hz, 1H), 3.64 (t, J=12.0 Hz, 1H), 3.48 (d, J=5.4 Hz, 6H), 3.42 (td, J=12.7, 4.1 Hz, 1H), 2.71 (s, 3H), 1.35 (d, J=6.7 Hz, 3H) ppm; MS (ES+) $C_{19}H_{24}N_6O_2S$ requires: 400, found: 401 $[M+H]^+$.

Example 5

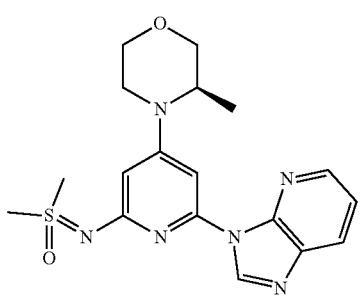 [SMILES: C[C@@H]1COCCN1c1cc(N=S(C)(C)=O)nc(-n2cnc3cccnc32)c1]

51

(R)-((6-(3H-Imidazo[4,5-b]pyridin-3-yl)-4-(3-methylmorpholino)pyridin-2-yl)imino)dimethyl-λ⁶-sulfanone Example 5 was synthesized per Example 4, with a modification in Step 3 where triethyl orthoformate was used instead of triethyl orthoacetate. $^1$H NMR (600 MHz, Methanol-d$_4$) δ 9.07 (s, 1H), 8.52 (d, J=4.9 Hz, 1H), 8.24 (d, J=8.1 Hz, 1H), 7.54-7.49 (m, 1H), 7.43 (s, 1H), 6.39 (s, 1H), 4.19-4.11 (m, 1H), 4.08-4.02 (m, 1H), 3.84 (d, J=11.7 Hz, 1H), 3.79 (d, J=11.4 Hz, 1H), 3.71-3.62 (m, 2H), 3.50 (d, J=3.5 Hz, 6H), 3.43-3.37 (m, 1H), 1.35 (d, J=6.8 Hz, 3H) ppm; MS (ES+) C$_{18}$H$_{22}$N$_6$O$_2$S requires: 386, found: 387 [M+H]⁺.

Example 6

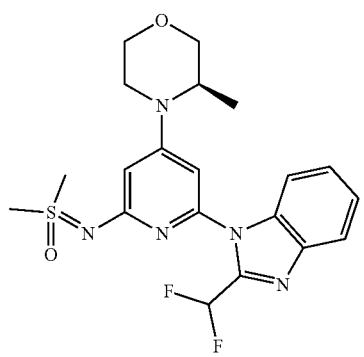 [SMILES: C[C@@H]1COCCN1c1cc(N=S(C)(C)=O)nc(-n2c(C(F)F)nc3ccccc32)c1]

(R)-((6-(2-(Difluoromethyl)-1H-benzo[d]imidazo-1-yl)-4-(3-methylmorpholino)pyridin-2-yl)imino)dimethyl-λ⁶-sulfanone

Step 1

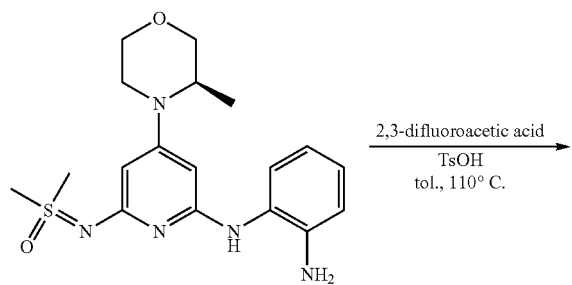

52

(R)-((6-((2-Aminophenyl)amino)-4-(3-methylmorpholino)pyridin-2-yl)imino)dimethyl-λ⁶-sulfanone was synthesized per Example 4, with a modification in Step 1 of substituting 3-nitropyridin-2-amine with 2-nitroaniline.

(R)-((6-(2-(Difluoromethyl)-1H-benzo[d]imidazol-1-yl)-4-(3-methylmorpholino)pyridin-2-yl)imino)dimethyl-λ⁶-sulfanone To a solution of (R)-((6-((2-Aminophenyl)amino)-4-(3-methylmorpholino)pyridin-2-yl)imino)dimethyl-λ⁶-sulfanone (50 mg, 0.13 mmol) in toluene (266 μL) were added 2,2-difluoroacetic acid (26 mg, 0.27 mmol) and TsOH (2.5 mg, 0.013 mmol) and the resulting mixture was stirred at 110° C. for 16 h. The mixture was cooled to room temperature, and concentrated under reduced pressure. The residue was purified by mass-triggered preparative HPLC (Mobile phase: A=0.1% TFA/H$_2$O, B=0.1% TFA/MeCN; Gradient: B=10-50%; 26 min; Column: XBridge C18, 5 μm, 19 mm×150 mm) to afford the title compound (28 mg, 32% yield) as a pale-yellow solid.

$^1$H NMR (600 MHz, Methanol-d$_4$) δ 7.84 (d, J=8.0 Hz, 1H), 7.57 (d, J=8.1 Hz, 1H), 7.51-7.44 (m, 2H), 7.32 (t, J=52.5 Hz, 1H), 6.94 (d, J=2.2 Hz, 1H), 6.46 (d, J=2.2 Hz, 1H), 4.11-4.06 (m, 1H), 4.02 (dd, J=11.2, 4.0 Hz, 1H), 3.82-3.74 (m, 2H), 3.66-3.60 (m, 2H), 3.44 (s, 6H), 3.32-3.29 (m, 1H), 1.32 (d, J=6.7 Hz, 3H); MS (ES⁺) C$_{20}$H$_{23}$F$_2$N$_5$O$_2$S requires: 435, found: 436 [M+H]⁺.

Example 7

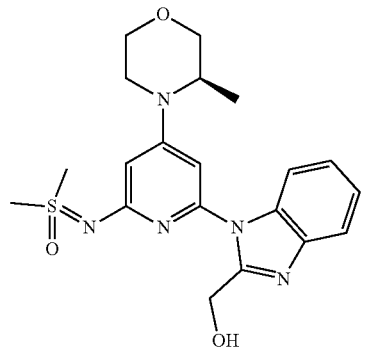 [SMILES: C[C@@H]1COCCN1c1cc(N=S(C)(C)=O)nc(-n2c(CO)nc3ccccc32)c1]

(R)-((6-(2-(Hydroxymethyl)-1H-benzo[d]imidazol-1-yl)-4-(3-methylmorpholino)pyridin-2-yl)imino)dimethyl-λ⁶-sulfanone

Step 1

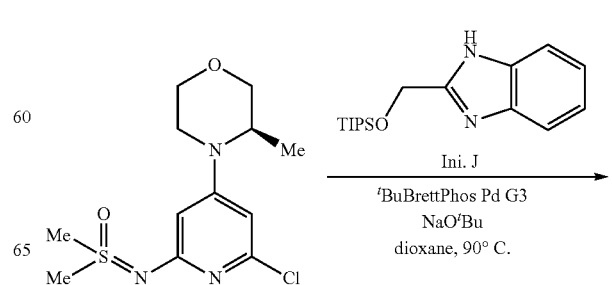

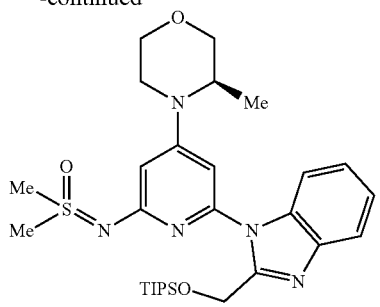

(R)-Dimethyl((4-(3-methylmorpholino)-6-(2-(((tri-isopropylsilyl)oxy)methyl)-1H-benzo[d]imidazol-1-yl)pyridin-2-yl)imino)-λ⁶-sulfanone A solution of (R)-((6-chloro-4-(3-methylmorpholino)pyridin-2-yl)imino)dimethyl-λ⁶-sulfanone (156 mg, 0.513 mmol) and Int. J (0188 mg, 0.616 mmol) in dioxane (5 mL) was degassed with N₂ for five minutes. NaOtBu (98 mg, 1.03 mmol) and t-BuBrettPhos Pd G3 pre-catalyst (44 mg, 0.051 mmol) were added and the mixture was sonicated for 1 min then heated at 90° C. for 70 minutes. The reaction was cooled to room temperature, diluted with ethyl acetate (20 mL), filtered through CELITE® and concentrated under reduced pressure. The residue was purified via flash chromatography (1:1:1 DCM:hexane:acetone with 1% Et₃N) to afford the title compound (178 mg, 61% yield) as a white solid. MS (ES⁺) C₂₉H₄₅N₅O₃SSi requires: 571, found: 572 [M+H]⁺.

Step 2

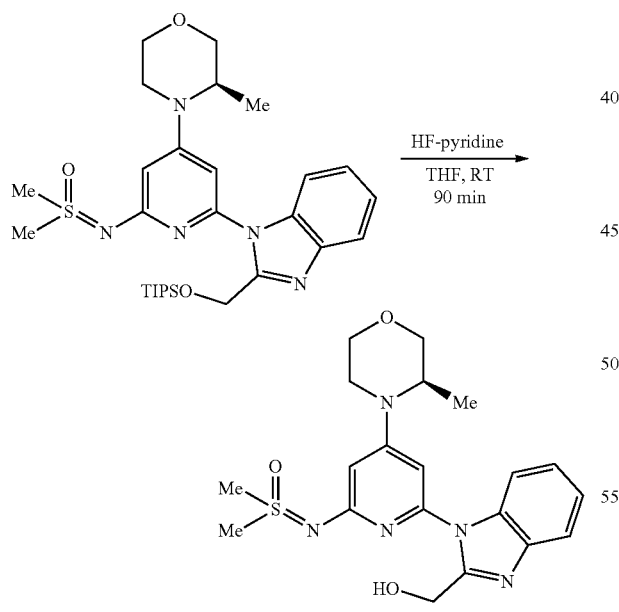

(R)-((6-(2-(hydroxymethyl)-1H-benzo[d]imidazol-1-yl)-4-(3-methylmorpholino)pyridin-2-yl)imino)dimethyl-λ⁶-sulfanone To a solution of the product from the previous step (0.28 g, 0.494 mmol) in THF (5 mL) in a Nalgene™ vial was added 30% HF-pyridine complex (1.0 mL) and the resulting mixture was stirred at room temperature for 90 min. Saturated aqueous NaHCO₃ (50 mL) was added and the resulting mixture stirred vigorously for 15 minutes. The aqueous layer was extracted with DCM (3×30 mL). The combine organic layers were dried over MgSO₄, filtered and concentrated under reduced pressure. The residue was purified by flash chromatography (2-10% MeOH/10% NH₄OH in DCM) to afford the title compound (156 mg, 74% yield) as a white solid.

¹H NMR (400 MHz, Chloroform-d) δ ppm 7.76-7.91 (m, 1H), 7.51-7.63 (m, 1H), 7.29-7.40 (m, 2H), 6.52 (d, J=2.26 Hz, 1H), 6.19 (d, J=2.01 Hz, 1H), 4.91 (s, 2H), 4.04 (dd, J=11.54, 3.51 Hz, 1H), 3.89 (q, J=6.78 Hz, 1H), 3.76-3.85 (m, 2H), 3.66 (td, J=11.80, 3.51 Hz, 1H), 3.42-3.43 (m, 1H), 3.20-3.22 (m, 1H), 3.20-3.44 (m, 6H), 1.31 (d, J=6.53 Hz, 3H) ppm; MS (ES⁺) C₂₀H₂₅N₅O₃S requires: 415, found: 416 [M+H]⁺.

Example 8

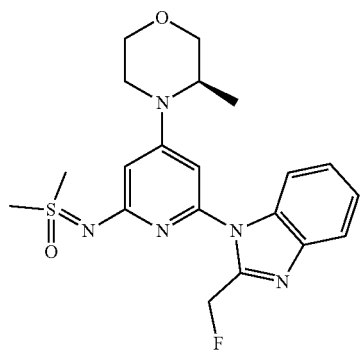 [SMILES: C[C@@H]1COCCN1c1cc(N=S(C)(C)=O)nc(-n2c(CF)nc3ccccc32)c1]

(R)-((6-(2-(Fluoromethyl)-1H-benzo[d]imidaazol-1-yl)-4-(3-methylmorpholino)pyridin-2-yl)imino)dimethyl-λ⁶-sulfanone

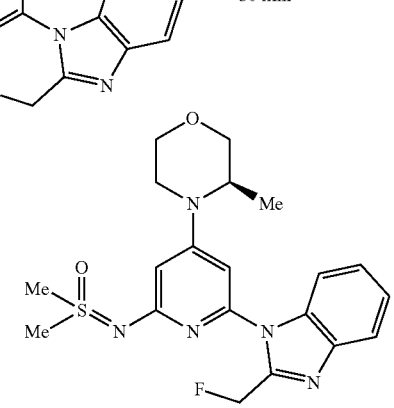

(R)-((6-(2-(Fluoromethyl)-1H-benzo[d]imidazol-1-yl)-4-(3-methylmorpholino)pyridin-2-yl)imino)dimethyl-λ⁶-sulfanone To a solution of (R)-((6-(2-(hydroxymethyl)-1H-benzo[d]imidazol-1-yl)-4-(3-methylmorpholino)pyridin-2-yl)imino)dimethyl-λ⁶-sulfanone (91 mg, 0.219 mmol) in DCM (5 mL) at 0° C. was added diethylaminosulfur trifluoride (DAST, 70 μL, 0.529 mmol) and the resulting mixture was allowed to warm to room temperature and stirred for 30 min. Saturated aqueous NaHCO₃ (25 mL) was added and the mixture was stirred vigorously for 15 minutes. The layers were separated and the aqueous layer was extracted with DCM (2×25 mL). The combined organic layers dried over MgSO₄, filtered and concentrated under reduced pressure. The residue was purified via flash chromatography (2-10% MeOH/10% NH₄OH in DCM with) to afford the title compound (48 mg 53% yield) as a white solid.

¹H NMR (400 MHz, Chloroform-d) δ ppm 7.83-7.98 (m, 1H), 7.72 (dd, J=6.53, 2.76 Hz, 1H), 7.34-7.48 (m, 2H), 6.54 (d, J=1.51 Hz, 1H), 6.21 (d, J=1.51 Hz, 1H), 5.89 (d, J=0.75 Hz, 1H), 5.78 (s, 1H), 4.04 (br dd, J=11.42, 3.39 Hz, 1H), 3.86-3.94 (m, 1H), 3.75-3.86 (m, 2H), 3.66 (td, J=11.80, 3.26 Hz, 1H), 3.21-3.42 (m, 8H), 1.30 (d, J=6.78 Hz, 3H) ppm; MS (ES⁺) C₂₀H₂₄FN₅O₂S requires: 417, found: 418 [M+H]⁺.

Example 9

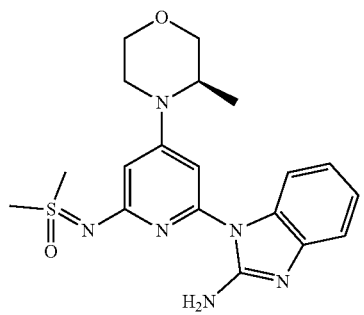 [SMILES: C[C@@H]1COCCN1c1cc(N=S(C)(C)=O)nc(-n2c(N)nc3ccccc32)c1]

(R)-((6-(2-Amino-1H-benzo[d]imidazol-1-yl)-4-(3-methylmorpholino)pyridin-2-yl)imino)dimethyl-λ⁶-sulfanone

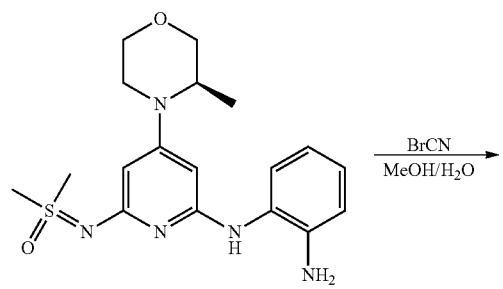

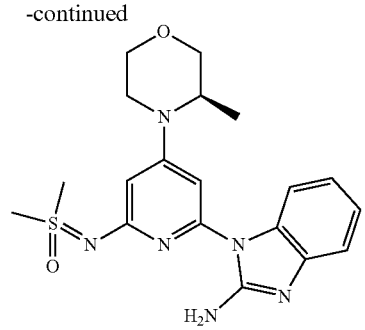

(R)-((6-((2-Aminophenyl)amino)-4-(3-methylmorpholino)pyridin-2-yl)imino)dimethyl-λ⁶-sulfanone was synthesized per Example 4, with a modification in Step 1 of substituting 3-nitropyridin-2-amine with 2-nitroaniline.

(R)-((6-(2-Amino-1H-benzo[d]imidazol-1-yl)-4-(3-methylmorpholino)pyridin-2-yl)imino)dimethyl-λ⁶-sulfanone To a solution of BrCN (68 mg, 0.64 mmol) in H₂O (3 mL) was added a solution of (R)-((6-((2-Aminophenyl)amino)-4-(3-methylmorpholino)pyridin-2-yl)imino)dimethyl-λ⁶-sulfanone (200 mg, 0.53 mmol) in MeOH (3 mL) dropwise. The resulting mixture was stirred at room temperature for 16 h. The mixture was concentrated under reduced pressure. The residue was partitioned between aqueous sat. NaHCO₃ (10 mL) and EtOAc (10 mL). The layers were separated and the aqueous layer was extracted with EtOAc (2×10 mL). The combined organic layers were dried over Na₂SO₄, filtered, concentrated under reduced pressure. The residue was purified by mass-triggered preparative HPLC (Mobile phase: A=0.1% TFA/H₂O, B=ACN; Gradient: B=10-90%; 17 min; Column: XBridge C8, 10 μm, 19 mm×250 mm) to provide the title compound (31 mg, 14%) as a gray solid.

¹H NMR (400 MHz, CDCl₃) δ 7.43 (t, J=7.8, 2H), 7.06 (t, J=7.5 Hz, 1H), 6.55 (s, 1H), 6.22 (s, 2H), 6.05 (s, 1H), 4.04 (d, J=8.4 Hz, 1H), 3.94-3.74 (m, 3H), 3.65 (t, J=10.4 Hz, 1H), 3.46-3.15 (m, 8H), 1.28 (d, J=6.6 Hz, 3H) ppm; MS (ES⁺) C₁₉H₂₄N₆O₂S requires: 400, found: 401 [M+H]⁺.

Example 10

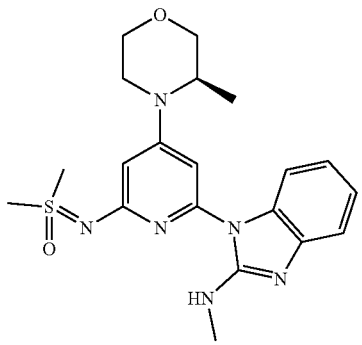 [SMILES: CNc1nc2ccccc2n1-c1cc(N2CCOC[C@H]2C)cc(N=S(C)(C)=O)n1]

(R)-Dimethyl((6-(2-(methylamino)-1H-benzo[d]imidazol-1-yl)-4-(3-methylmorpholino)pyridin-2-yl)imino)-λ⁶-sulfanone

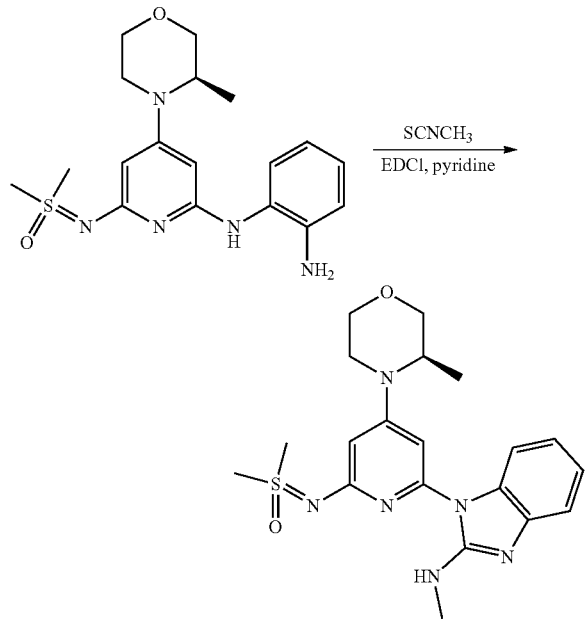

(R)-((6-((2-Aminophenyl)amino)-4-(3-methylmorpholino)pyridin-2-yl)imino)dimethyl-λ⁶-sulfanone was synthesized according to Example 4, with a modification in Step 1 of substituting 3-nitropyridin-2-amine with 2-nitroaniline.

(R)-Dimethyl((6-(2-(methylamino)-1H-benzo[d]imidazol-1-yl)-4-(3-methylmorpholino)pyridin-2-yl)imino)-λ⁶-sulfanone To a solution of (R)-((6-((2-Aminophenyl)amino)-4-(3-methylmorpholino)pyridin-2-yl)imino)dimethyl-λ⁶-sulfanone (100 mg, 0.266 mmol) in pyridine (5 mL) was added isothiocyanatomethane (21 mg, 0.29 mmol). The mixture was heated at 80° C. and stirred for 30 min. EDCI (71 mg, 0.37 mmol) was added, and the reaction mixture was stirred at 80° C. for an additional 16 h. The reaction mixture was cooled to room temperature, water was added (10 mL), and the aqueous layer was extracted with EtOAc (2×10 mL). The combined organic layers were dried over $Na_2SO_4$, filtered, and concentrated under reduced pressure. The residue was purified by mass-triggered preparative HPLC (Mobile phase: A=0.1% TFA/$H_2O$, B=ACN; Gradient: B=10-90%; 17 min; Column: XBridge $C_8$, 10 m, 19 mm×250 mm) to afford the title compound (37 mg, 34%) as a white solid.

$^1$H NMR (400 MHz, $CDCl_3$) δ 7.74 (s, 1H), 7.51 (d, J=7.6 Hz, 1H), 7.40 (d, J=7.6 Hz, 1H), 7.15 (t, J=7.5 Hz, 1H), 7.03 (t, J=7.5 Hz, 1H), 6.55 (s, 1H), 6.02 (s, 1H), 4.03 (d, J=9.2 Hz, 1H), 3.92-3.73 (m, 3H), 3.65 (t, J=10.2 Hz, 1H), 3.43-3.20 (m, 8H), 3.15 (d, J=4.5 Hz, 3H), 1.27 (d, J=6.5 Hz, 3H) ppm; MS (ES$^+$) $C_{20}H_{26}N_6O_2S$ requires: 414, found: 415 [M+H]$^+$.

The compounds reported in Table 1 were synthesized using the methods described above as indicated in the procedure column ("Proc."). The appropriate sulfoximines were prepared as described for Intermediates C. The "Ex No." corresponds to the example numbers above, or to further compounds using the same methods. "MW" is the calculated molecular weight, and "[M+H]" is the weight of the molecular ion found via mass spectroscopy.

TABLE 1

| Ex. No. | Structure | IUPAC Name | MW/[M + H] | Proc. |
|---|---|---|---|---|
| 1 | 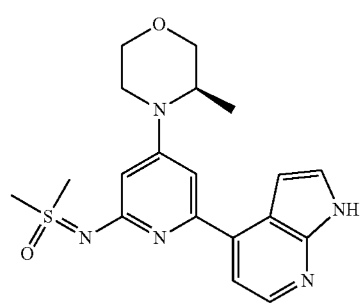 [SMILES: C[C@@H]1COCCN1c1cc(N=S(C)(C)=O)nc(-c2ccnc3[nH]ccc23)c1] | (R)-Dimethyl((4-(3-methylmorpholino)-6-(1H-pyrrolo[2,3-b]pyridin-4-yl)pyridin-2-yl)imino)-λ⁶-sulfanone | 385/386 | 1 |
| 2 | 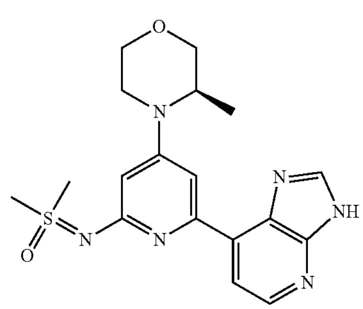 [SMILES: C[C@@H]1COCCN1c1cc(N=S(C)(C)=O)nc(-c2ccnc3[nH]cnc23)c1] | (R)-((6-(3H-imidazo[4,5-b]pyridin-7-yl)-4-(3-methylmorpholino)pyridin-2-yl)imino)dimethyl-λ⁶-sulfanone | 386/387 | 2 |

TABLE 1-continued

| Ex. No. | Structure | IUPAC Name | MW/ [M + H] | Proc. |
|---|---|---|---|---|
| 3a, 3b | 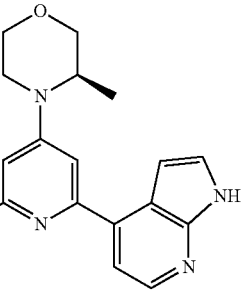 | Cyclopropyl(methyl)((4-((R)-3-methylmorpholino)-6-(1H-pyrrolo[2,3-b] pyridin-4-yl)pyridin-2-yl)imino)-$\lambda^6$-sulfanone | 412/ 413 | 3 |
| 4 | 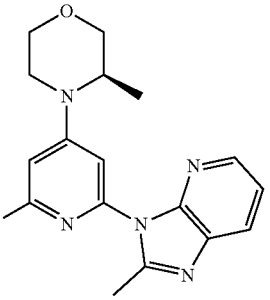 | (R)-dimethyl((6-(2-methyl-3H-imidazo[4,5-b]pyridin-3-yl)-4-(3-methylmorpholino)pyridin-2-yl)imino)-$\lambda^6$-sulfanone | 401/ 402 | 4 |
| 5 | 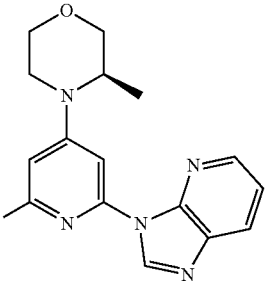 | (R)-((6-(3H-imidazo[4,5-b]pyridin-3-yl)-4-(3-methylmorpholino)pyridin-2-yl)imino)dimethyl-$\lambda^6$-sulfanone | 386/ 387 | 4 |
| 6 | 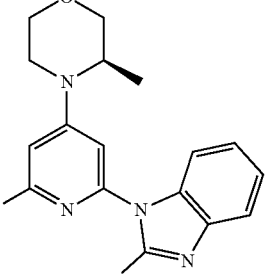 | (R)-((6-(2-(difluoromethyl)-1H-benzo[d]imidazol-1-yl)-4-(3-methylmorpholino)pyridin-2-yl)imino)dimethyl-$\lambda^6$-sulfanone | 435/ 436 | 4 |
| 7 | 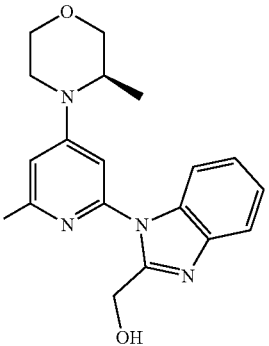 | (R)-((6-(2-(Hydroxymethyl)-1H-benzo[d]imidazol-1-yl)-4-(3-methylmorpholino)pyridin-2-yl)imino)dimethyl-$\lambda^6$-sulfanone | 571/ 572 | 7 |

TABLE 1-continued

| Ex. No. | Structure | IUPAC Name | MW/ [M + H] | Proc. |
|---|---|---|---|---|
| 8 | 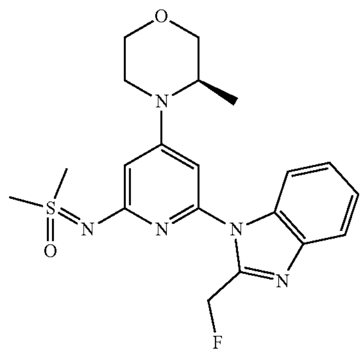 [SMILES: C[C@@H]1COCCN1c1cc(N=S(C)(C)=O)nc(-n2c(CF)nc3ccccc32)c1] | (R)-((6-(2-(Fluoromethyl)-1H-benzo[dr]imidazol-1-yl)-4-(3-methylmorpholino)pyridin-2-yl)imino)dimethyl-$\lambda^6$-sulfanone | 417/ 418 | 8 |
| 9 | 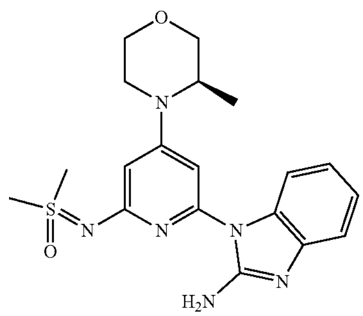 [SMILES: C[C@@H]1COCCN1c1cc(N=S(C)(C)=O)nc(-n2c(N)nc3ccccc32)c1] | (R)-((6-(2-Amino-1H-benzo[d]imidazol-1-yl)-4-(3-methylmorpholino)pyridin-2-yl)imino)dimethyl-$\lambda^6$-sulfanone | 400/ 401 | 9 |
| 10 | 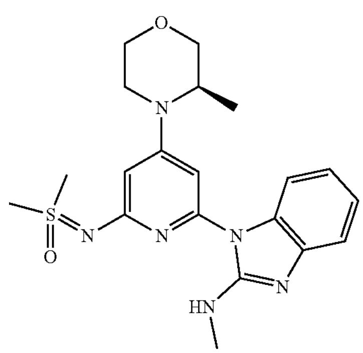 [SMILES: CNc1nc2ccccc2n1-c1cc(N2CCOC[C@H]2C)cc(N=S(C)(C)=O)n1] | (R)-Dimethyl((6-(2-(methylamino)-1H-benzo[d]imidazol-1-yl)-4-(3-methylmorpholino)pyridin-2-yl)imino)-$\lambda^6$-sulfanone | 414/ 415 | 10 |
| 11 | 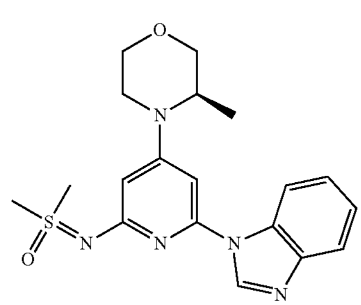 [SMILES: C[C@@H]1COCCN1c1cc(N=S(C)(C)=O)nc(-n2cnc3ccccc32)c1] | (R)-((6-(1H-benzo[d]imidazol-1-yl)-4-(3-methylmorpholino)pyridin-2-yl)imino)dimethyl-$\lambda^6$-sulfanone | 385/ 386 | 5 |

TABLE 1-continued

| Ex. No. | Structure | IUPAC Name | MW/ [M + H] | Proc. |
|---|---|---|---|---|
| 12 | 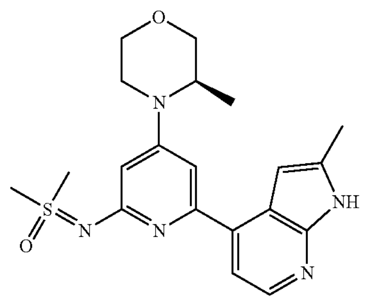 | (R)-dimethyl((6-(2-methyl-1H-pyrrolo[2,3-b]pyridin-4-yl)-4-(3-methylmorpholino)pyridin-2-yl)imino)-λ⁶-sulfanone | 399/ 400 | 1 |
| 13 | 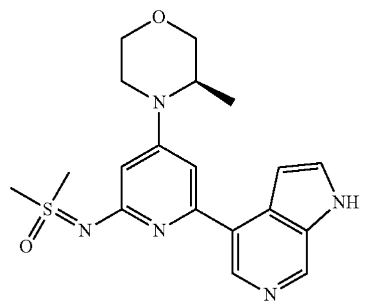 [SMILES: C[C@@H]1COCCN1c1cc(N=S(C)(C)=O)nc(-c2cncc3[nH]ccc23)c1] | (R)-dimethyl((4-(3-methylmorpholino)-6-(1H-pyrrolo[2,3-c]pyridin-4-yl)pyridin-2-yl)imino)-λ⁶-sulfanone | 385/ 386 | 1 |
| 14 | 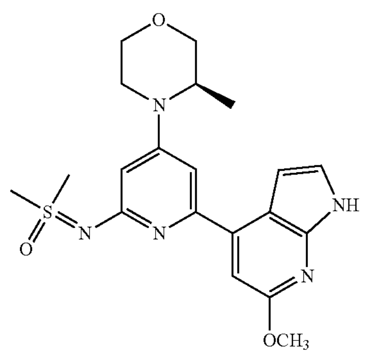 [SMILES: COc1cc(-c2cc(N3CCOC[C@H]3C)cc(N=S(C)(C)=O)n2)c2cc[nH]c2n1] | (R)-((6-(6-methoxy-1H-pyrrolo[2,3-b]pyridin-4-yl)-4-(3-methylmorpholino)pyridin-2-yl)imino)dimethyl-λ⁶-sulfanone | 415/ 416 | 1 |
| 15 | 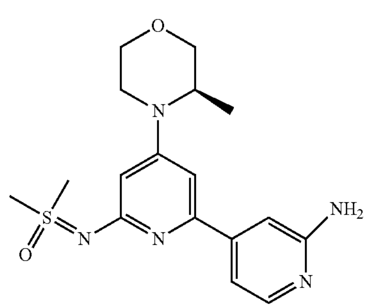 [SMILES: C[C@@H]1COCCN1c1cc(N=S(C)(C)=O)nc(-c2ccnc(N)c2)c1] | (R)-((2'-amino-4-(3-methylmorpholino)-[2,4'-bipyridin]-6-yl)imino)dimethyl-λ⁶-sulfanone | 361/ 362 | 1 |
| 16 | 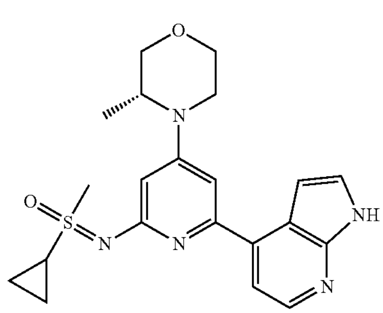 [SMILES: C[C@@H]1COCCN1c1cc(N=S(C)(=O)C2CC2)nc(-c2ccnc3[nH]ccc23)c1] | cyclopropyl(methyl)((4-((R)-3-methylmorpholino)-6-(1H-pyrrolo[2,3-b]pyridin-4-yl)pyridin-2-yl)imino)-λ⁶-sulfanone | 411/ 412 | 1 |

TABLE 1-continued

| Ex. No. | Structure | IUPAC Name | MW/ [M + H] | Proc. |
|---|---|---|---|---|
| 17 | 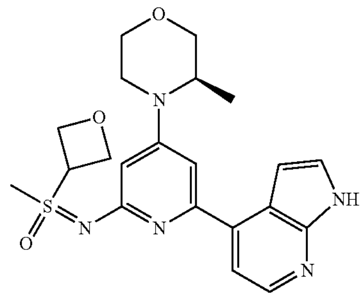 [SMILES: C[C@@H]1COCCN1c1cc(N=S(C)(=O)C2COC2)nc(-c2ccnc3[nH]ccc23)c1] | methyl((4-((R)-3-methylmorpholino)-6-(1H-pyrrolo[2,3-b]pyridin-4-yl)pyridin-2-yl)imino)(oxetan-3-yl)-λ⁶-sulfanone | 427/ 428 | 1 |
| 18 | 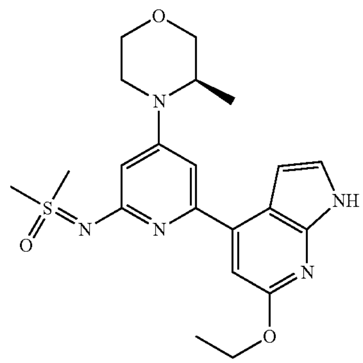 [SMILES: CCOc1cc(-c2cc(N3CCOC[C@H]3C)cc(N=S(C)(C)=O)n2)c2cc[nH]c2n1] | (R)-((6-(6-ethoxy-1H-pyrrolo[2,3-b]pyridin-4-yl)-4-(3-methylmorpholino)pyridin-2-yl)imino)dimethyl-λ⁶-sulfanone | 429/ 430 | 1 |
| 20 | 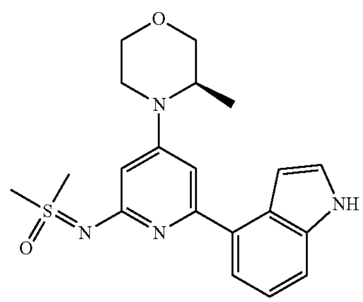 [SMILES: C[C@@H]1COCCN1c1cc(N=S(C)(C)=O)nc(-c2cccc3[nH]ccc23)c1] | (R)-((6-(1H-indol-4-yl)-4-(3-methylmorpholino)pyridin-2-yl)imino)dimethyl-λ⁶-sulfanone | 384/ 385 | 1 |
| 21 | 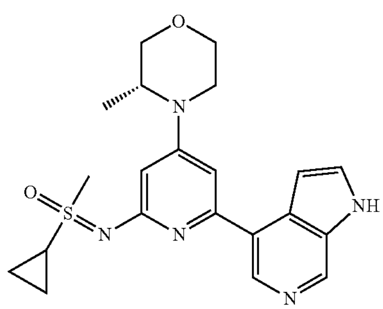 [SMILES: C[C@@H]1COCCN1c1cc(N=S(C)(=O)C2CC2)nc(-c2cncc3[nH]ccc23)c1] | cyclopropyl(methyl)((4-((R)-3-methylmorpholino)-6-(1H-pyrrolo[2,3-c]pyridin-4-yl)pyridin-2-yl)imino)-λ⁶-sulfanone | 411/ 412 | 1 |
| 23 | 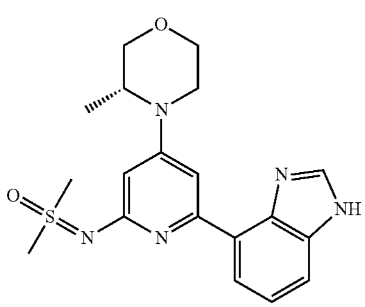 [SMILES: C[C@@H]1COCCN1c1cc(N=S(C)(C)=O)nc(-c2cccc3[nH]cnc23)c1] | (R)-((6-(1H-benzo[d]imidazol-4-yl)-4-(3-methylmorpholino)pyridin-2-yl)imino)dimethyl-λ⁶-sulfanone | 385/ 386 | 2 |

TABLE 1-continued

| Ex. No. | Structure | IUPAC Name | MW/ [M + H] | Proc. |
|---|---|---|---|---|
| 24 | 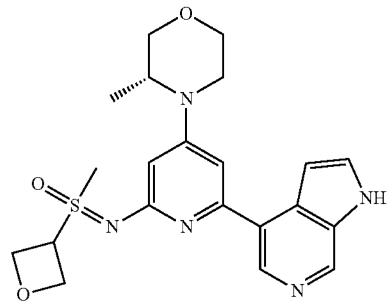 [SMILES: C[C@@H]1COCCN1c1cc(N=S(C)(=O)C2COC2)nc(-c2cncc3[nH]ccc23)c1] | methyl((4-((R)-3-methylmorpholino)-6-(1H-pyrrolo[2,3-c]pyridin-4-yl)pyridin-2-yl)imino)(oxetan-3-yl)-$\lambda^6$-sulfanone | 427/ 428 | 1 |
| 25 | 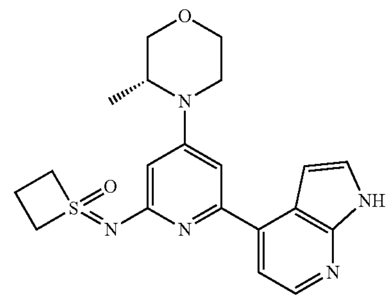 [SMILES: C[C@@H]1COCCN1c1cc(N=S2(=O)CCC2)nc(-c2ccnc3[nH]ccc23)c1] | (R)-1-((4-(3-methylmorpholino)-6-(1H-pyrrolo[2,3-b]pyridin-4-yl)pyridin-2-yl)imino)-1-$\lambda^6$-thietane 1-oxide | 397/ 398 | 1 |
| 26 | 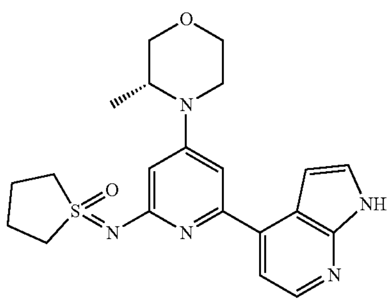 [SMILES: C[C@@H]1COCCN1c1cc(N=S2(=O)CCCC2)nc(-c2ccnc3[nH]ccc23)c1] | (R)-1-((4-(3-methylmorpholino)-6-(1H-pyrrolo[2,3-b]pyridin-4-yl)pyridin-2-yl)imino)tetrahydro-1H-1-$\lambda^6$-thiophene 1-oxide | 411/ 412 | 1 |
| 27 | 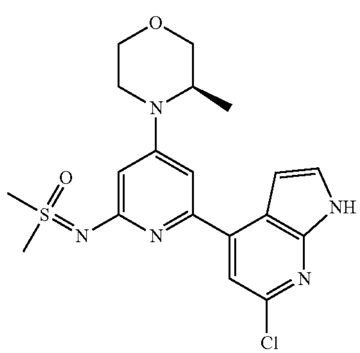 [SMILES: C[C@@H]1COCCN1c1cc(N=S(C)(C)=O)nc(-c2cc(Cl)nc3[nH]ccc23)c1] | (R)-((6-(6-chloro-1H-pyrrolo[2,3-b]pyridin-4-yl)-4-(3-methylmorpholino)pyridin-2-yl)imino)dimethyl-$\lambda^6$-sulfanone | 419/ 420 | 1 |
| 28 | 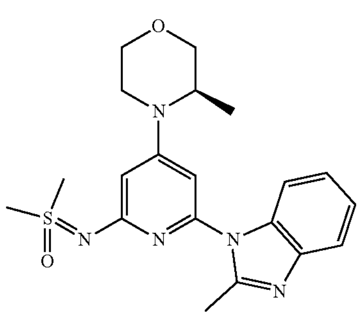 [SMILES: Cc1nc2ccccc2n1-c1cc(N2CCOC[C@H]2C)cc(N=S(C)(C)=O)n1] | (R)-dimethyl((6-(2-methyl-1H-benzo[d]imidazol-1-yl)-4-(3-methylmorpholino)pyridin-2-yl)imino)-$\lambda^6$-sulfanone | 399/ 400 | 4 |

TABLE 1-continued

| Ex. No. | Structure | IUPAC Name | MW/[M + H] | Proc. |
|---|---|---|---|---|
| 29 | 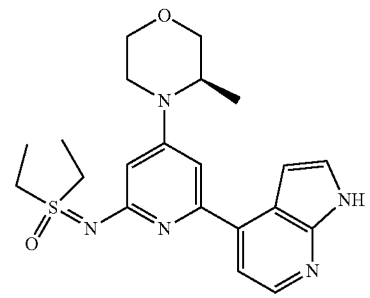 [SMILES: CCS(=O)(CC)=Nc1cc(N2CCOC[C@H]2C)cc(-c2ccnc3[nH]ccc23)n1] | diethyl({6-[(3R)-3-methylmorpholin-4-yl]-2-{1H-pyrrolo[2,3-b]pyridin-4-yl}pyrimidin-4-yl}imino)-λ⁶-sulfanone | 414/415 | 1 |
| 30 | 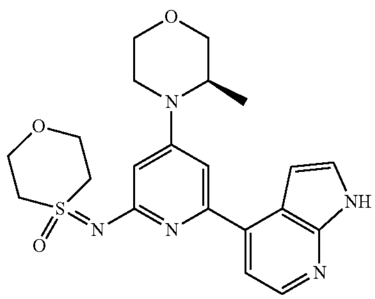 [SMILES: C[C@@H]1COCCN1c1cc(N=S2(=O)CCOCC2)nc(-c2ccnc3[nH]ccc23)c1] | 1-({6-[(3R)-3-methylmorpholin-4-yl]-2-{1H-pyrrolo[2,3-b]pyridin-4-yl}pyrimidin-4-yl}imino)-λ⁶-thian-1-one | 426/427 | 1 |
| 31 | 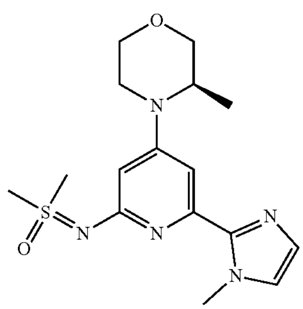 [SMILES: C[C@@H]1COCCN1c1cc(N=S(C)(C)=O)nc(-c2nccn2C)c1] | (R)-dimethyl((6-(1-methyl-1H-imidazol-2-yl)-4-(3-methylmorpholino)pyridin-2-yl)imino)-λ⁶-sulfanone | 349/350 | 1 |
| 32 | 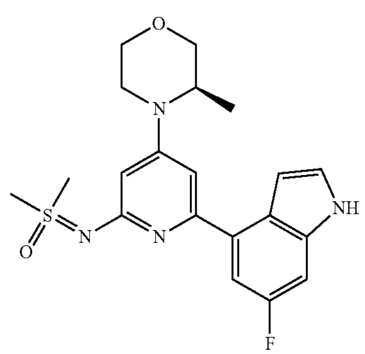 [SMILES: C[C@@H]1COCCN1c1cc(N=S(C)(C)=O)nc(-c2cc(F)cc3[nH]ccc23)c1] | (R)-((6-(6-fluoro-1H-indol-4-yl)-4-(3-methylmorpholino)pyridin-2-yl)imino)dimethyl-λ⁶-sulfanone | 402/403 | 1 |
| 33 | 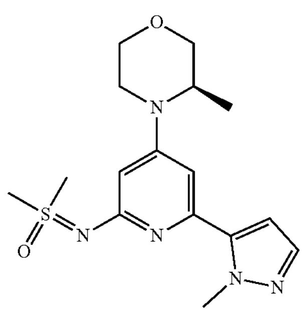 [SMILES: C[C@@H]1COCCN1c1cc(N=S(C)(C)=O)nc(-c2ccnn2C)c1] | (R)-dimethyl((6-(1-methyl-1H-pyrazol-5-yl)-4-(3-methylmorpholino)pyridin-2-yl)imino)-λ⁶-sulfanone | 349/350 | 1 |

TABLE 1-continued

| Ex. No. | Structure | IUPAC Name | MW/ [M + H] | Proc. |
|---|---|---|---|---|
| 34 | 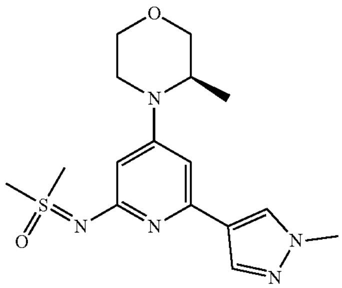 | (R)-dimethyl((6-(1-methyl-1H-pyrazol-4-yl)-4-(3-methylmorpholino)pyridin-2-yl)imino)-$\lambda^6$-sulfanone | 349/ 350 | 1 |
| 35 | 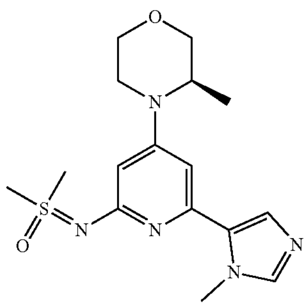 [SMILES: C[C@@H]1COCCN1c1cc(N=S(C)(C)=O)nc(-c2cncn2C)c1] | (R)-dimethyl((6-(1-methyl-1H-imidazol-5-yl)-4-(3-methylmorpholino)pyridin-2-yl)imino)-$\lambda^6$-sulfanone | 349/ 350 | 1 |
| 36 | 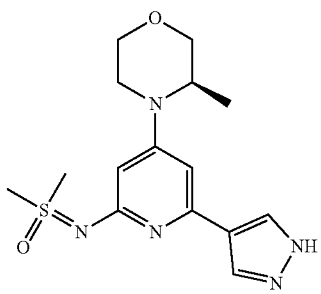 [SMILES: C[C@@H]1COCCN1c1cc(N=S(C)(C)=O)nc(-c2cn[nH]c2)c1] | (R)-dimethyl((4-(3-methylmorpholino)-6-(1H-pyrazol-4-yl)pyridin-2-yl)imino)-$\lambda^6$-sulfanone | 335/ 336 | 1 |
| 37 | 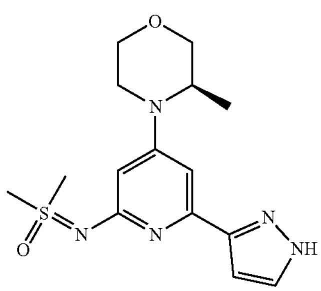 [SMILES: C[C@@H]1COCCN1c1cc(N=S(C)(C)=O)nc(-c2cc[nH]n2)c1] | (R)-dimethyl((4-(3-methylmorpholino)-6-(1H-pyrazol-3-yl)pyridin-2-yl)imino)-$\lambda^6$-sulfanone | 335/ 336 | 1 |
| 38 | 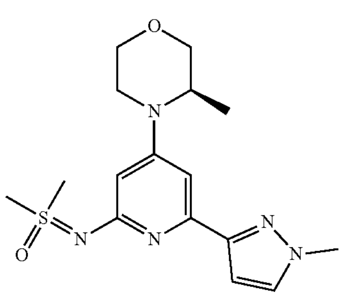 | (R)-dimethyl((6-(1-methyl-1H-pyrazol-3-yl)-4-(3-methylmorpholino)pyridin-2-yl)imino)-$\lambda^6$-sulfanone | 349/ 350 | 1 |

TABLE 1-continued

| Ex. No. | Structure | IUPAC Name | MW/ [M + H] | Proc. |
|---|---|---|---|---|
| 39 | 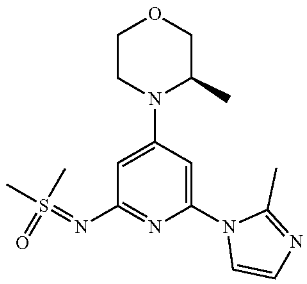 [SMILES: Cc1nccn1-c1cc(N2CCOC[C@H]2C)cc(N=S(C)(C)=O)n1] | (R)-dimethyl((6-(2-methyl-1H-imidazol-1-yl)-4-(3-methylmorpholino)pyridin-2-yl)imino)-λ⁶-sulfanone | 349/ 350 | 1 |

The following compounds can generally be made using the methods known in the art and described above:

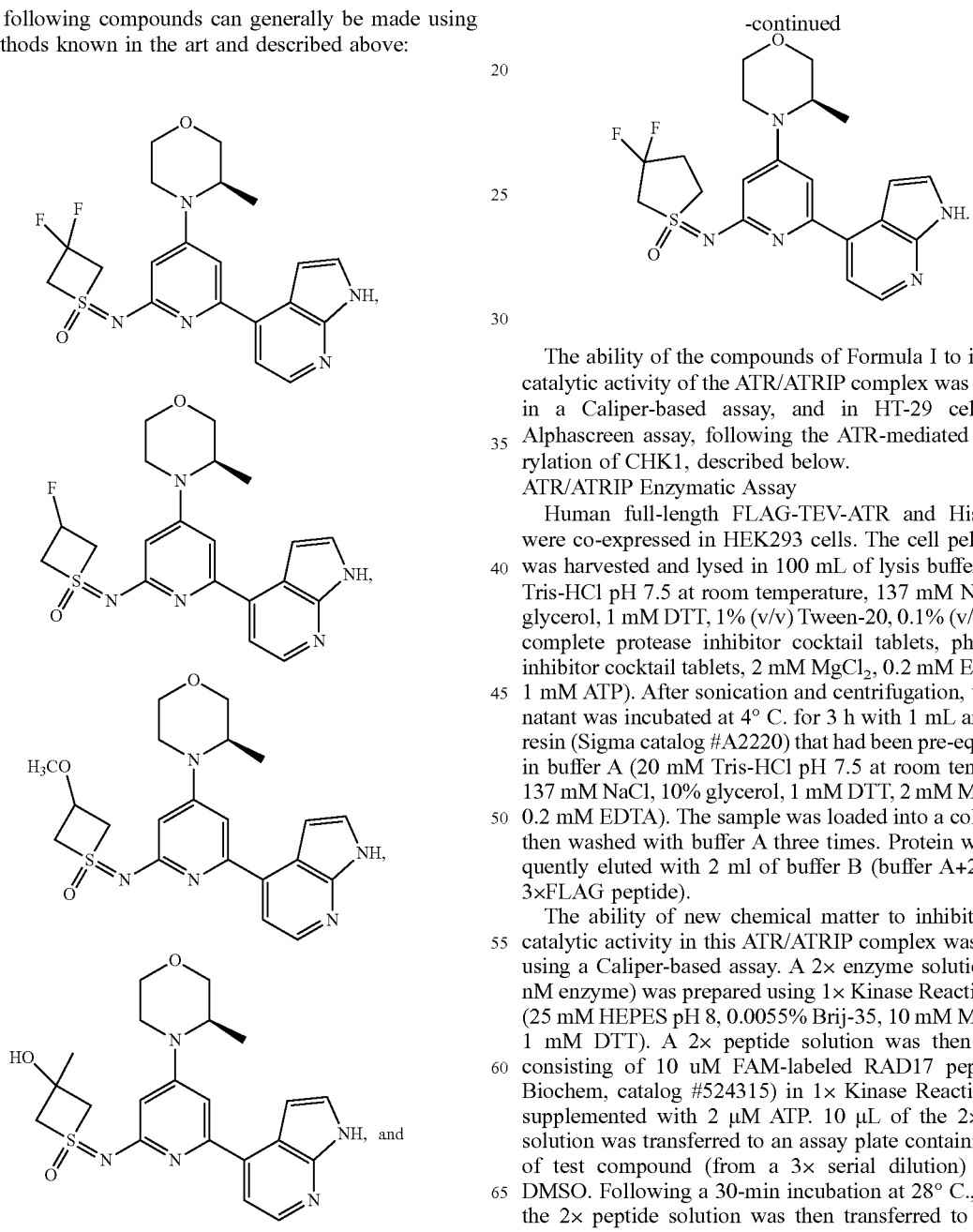

The ability of the compounds of Formula I to inhibit the catalytic activity of the ATR/ATRIP complex was measured in a Caliper-based assay, and in HT-29 cells in an Alphascreen assay, following the ATR-mediated phosphorylation of CHK1, described below.

ATR/ATRIP Enzymatic Assay

Human full-length FLAG-TEV-ATR and His6-ATRIP were co-expressed in HEK293 cells. The cell pellet (20 g) was harvested and lysed in 100 mL of lysis buffer (20 mM Tris-HCl pH 7.5 at room temperature, 137 mM NaCl, 10% glycerol, 1 mM DTT, 1% (v/v) Tween-20, 0.1% (v/v) NP-40, complete protease inhibitor cocktail tablets, phosphatase inhibitor cocktail tablets, 2 mM $MgCl_2$, 0.2 mM EDTA, and 1 mM ATP). After sonication and centrifugation, the supernatant was incubated at 4° C. for 3 h with 1 mL anti-FLAG resin (Sigma catalog #A2220) that had been pre-equilibrated in buffer A (20 mM Tris-HCl pH 7.5 at room temperature, 137 mM NaCl, 10% glycerol, 1 mM DTT, 2 mM $MgCl_2$, and 0.2 mM EDTA). The sample was loaded into a column, and then washed with buffer A three times. Protein was subsequently eluted with 2 ml of buffer B (buffer A+200 µg/ml 3×FLAG peptide).

The ability of new chemical matter to inhibit the ATR catalytic activity in this ATR/ATRIP complex was assessed using a Caliper-based assay. A 2× enzyme solution (i.e., 4 nM enzyme) was prepared using 1× Kinase Reaction Buffer (25 mM HEPES pH 8, 0.0055% Brij-35, 10 mM $MnCl_2$, and 1 mM DTT). A 2× peptide solution was then prepared consisting of 10 uM FAM-labeled RAD17 peptide (GL Biochem, catalog #524315) in 1× Kinase Reaction Buffer supplemented with 2 µM ATP. 10 µL of the 2× enzyme solution was transferred to an assay plate containing 60 nL of test compound (from a 3× serial dilution) in 100% DMSO. Following a 30-min incubation at 28° C., 10 µL of the 2× peptide solution was then transferred to the same assay plate. The reaction incubated at 28° C. for 6 h. After adding 30 μL stop buffer (100 mM HEPES pH 7.5, 0.015% Brij-35, 0.2% Coating-3 Reagent (PerkinElmer, catalog #PN760050), and 50 mM EDTA), data were collected on a Caliper instrument. Conversion values were converted to inhibition values via the following equation: % inhibition= (max−conversion)/(max−min)*100, wherein "max" corresponds to the DMSO control, and "min" corresponds to the low control. $IC_{50}$ values were calculated using the following equation in XLFit: Y=Bottom+(Top−Bottom)/1+($IC_{50}$/X)^HillSlope).

TABLE 2

ATR/ATRIP Enzyme $IC_{50}$ values

| Example No. | ATR $IC_{50}$ (nM) |
|---|---|
| 1 | 10 |
| 2 | 118 |
| 3a | 31 |
| 3b | 4 |
| 4 | 986 |
| 5 | 44 |
| 6 | 5 |
| 7 | 16 |
| 8 | 5 |
| 9 | 1 |
| 10 | 1 |
| 11 | 9 |
| 12 | 11 |
| 13 | 9 |
| 14 | 48 |
| 15 | 372 |
| 16 | 8 |
| 17 | 12 |
| 18 | 29 |
| 19 | 4 |
| 20 | 12 |
| 21 | 9 |
| 22 | 6 |
| 23 | 8 |
| 24 | 24 |
| 25 | 9 |
| 26 | 8 |
| 27 | 30 |
| 28 | 24 |
| 29 | 2 |
| 30 | 8 |
| 31 | 3469 |
| 32 | 4 |
| 33 | 1848 |
| 34 | 3442 |
| 35 | — |
| 36 | — |
| 37 | — |
| 38 | — |
| 39 | 3469 | pCHK1 Cellular Assay

Inhibitors of ATR kinase effectively inhibiting the ATR-driven phosphorylation of the downstream target Chk1 kinase at Serine 345, following the addition of 4-nitroquinoline N-oxide, a chemical used to induce DNA damage. Cellular $IC_{50}$ for the inhibitors of ATR described herein were measured in HT-29 colorectal adenocarcinoma cells. HT-29 cells were routinely maintained in McCoy's 5A media (ATCC Catalog #30-2007) supplemented with 10% fetal bovine serum (Sigma Catalog #$F_{2442}$) and 1× Penicillin-Streptomycin (Gibco Catalog #15140-122) using a humidified incubator (37° C., 5% $CO_2$, and ambient 02).

To prepare the CHK1 (p-Ser345) ALPHASCREEN® SUREFIRE® assay, cells were harvested and resuspended in McCoy's 5A media supplemented with 10% fetal bovine serum and 1× Penicillin-Streptomycin. Cells were seeded onto a 384-well black CELLSTAR® Tissue Culture Plate (VWR Catalog #89085-314) at a density of 13,000 cells/well in a volume of 40 μL. The microplate was incubated overnight (approximately 20 hours) at 37° C. with 5% $CO_2$ and ambient $O_2$. Stock solutions of the test compounds were prepared in 100% DMSO (Sigma, Catalog #D2650) and serially diluted 1:3 using 100% DMSO. Compounds were additionally diluted 1:33 in culture medium, and 10 μL/well were transferred to the tissue culture plate. Following the compound addition, the microplate was incubated at 37° C. for 90 minutes. 10 μL 4-nitroquinoline N-oxide (Sigma Aldrich Catalog #N8141-1G) diluted in media (final concentration 12 μM) were added to the tissue culture plate followed by a 120-min incubation at 37° C. The cells were then washed with PBS and lysed using 10 μL/well SUREFIRE® Kit lysis buffer diluted to 1× in water (PerkinElmer Catalog #TGRCHK1S$_{50}$K), with mixing on an orbital shaker at 500 rpm for 20 min at room temperature. Lysates were frozen at −20 OC overnight.

4 μL/well of lysate was then transferred from the tissue culture plate to a 384-well, white, low volume, PROXIPLATE™ (PerkinElmer Catalog #600828). 5 μL/well of the acceptor bead solution, prepared by diluting SUREFIRE® Kit activation buffer (PerkinElmer Catalog #TGRCHK1S50K) and ALPHASCREEN® Protein A acceptor beads (PerkinElmer Catalog #6760617R) in SUREFIRE® Kit reaction buffer (PerkinElmer Catalog #TGRCHK1S50K), were added to the lysates under subdued light and incubated at room temperature for 120 min. 2 μL/well of the donor bead solution, prepared by diluting ALPHASCREEN® Streptavidin donor beads (PerkinElmer Catalog #6760617R) in SUREFIRE® Kit dilution buffer (PerkinElmer Catalog #TGRCHK1S50K), were added under subdued light and incubated at room temperature for an addition 120 minutes. The pCHK1 ALPHASCREEN® signal was measured using an ENVISION® plate reader (PerkinElmer). $IC_{50}$ values were calculated using a four-parameter logistic curve fit using Genedata Screener software. Percent of control for each compound concentration was calculated by the following formula: 100*(Compound−Min)/(Max−Min), where "Max" is the high control, DMSO, and "Min" is the low control, 5 μM ATR inhibitor.

TABLE 3 pCHK1 $IC_{50}$ values

| Example No. | Cell $IC_{50}$ (nM) |
|---|---|
| 1 | 288 |
| 2 | 804 |
| 3a | 2229 |
| 3b | 196 |
| 4 | 10000 |
| 5 | 10000 |
| 6 | 2320 |
| 7 | 8625 |
| 8 | 3332 |
| 9 | 159 |
| 10 | 35 |
| 11 | 3160 |
| 12 | 99 |
| 13 | 232 |
| 14 | 3649 |
| 15 | 875 |
| 16 | 272 |
| 17 | 638 |
| 18 | 470 |
| 19 | 195 |
| 20 | 364 |
| 21 | 110 |
| 22 | 282 |

TABLE 3-continued

| pCHK1 IC$_{50}$ values | |
|---|---|
| Example No. | Cell IC$_{50}$ (nM) |
| 23 | 467 |
| 24 | 470 |
| 25 | 767 |
| 26 | 701 |
| 27 | 660 |
| 28 | 10000 |
| 29 | 44 |
| 30 | 86 |
| 31 | 3055 |
| 32 | 195 |
| 33 | 615 |
| 34 | 10000 |
| 35 | 9619 |
| 36 | 5555 |
| 37 | 8210 |
| 38 | 10000 |
| 39 | 3055 |

Formulation Examples

The pharmaceutical compositions may be prepared by methods disclosed herein and known in the art.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula (I):

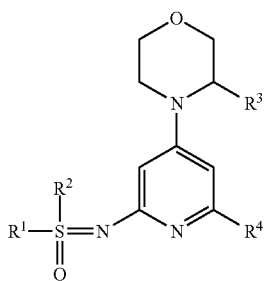

(I)

or a salt thereof, wherein:
R$^1$ and R$^2$ are independently chosen from C$_{1-4}$ alkyl, C$_{1-4}$ haloalkyl, C$_{3-6}$ cycloalkyl, C$_{3-6}$ heterocycloalkyl, aryl, and heteroaryl, each of which is optionally substituted with one or more R$^5$ groups, or R$^1$ and R$^2$, together with the sulfur to which they are both attached, form a heterocycloalkyl ring which is optionally substituted with one or more R$^5$ groups;
R$^3$ is chosen from hydrogen, C$_{1-6}$ alkyl, and C$_{1-6}$ haloalkyl;
R$^4$ is chosen from C$_{5-10}$ aryl and 5-10 membered heteroaryl, each of which is optionally substituted with one or more R$^6$ groups;
each R$^5$ is independently chosen from NR$^8$R$^9$, halogen, cyano, hydroxy, oxo, alkyl, haloalkyl, cycloalkyl, heterocycloalkyl, hydroxyalkyl, OR$^8$, NR$^7$C(O)R$^8$, NR$^7$C(O)OR$^8$, NR$^7$C(O)NR$^8$R$^9$, C(O)R$^8$, C(O)OR$^8$, and C(O)NR$^8$R$^9$;
each R$^6$ is independently chosen from NR$^{11}$R$^{12}$, halogen, cyano, hydroxy, oxo, alkyl, haloalkyl, cycloalkyl, heterocycloalkyl, hydroxyalkyl, OR$^{11}$, NR$^{10}$C(O)R$^{11}$, NR$^{10}$C(O)OR$^{11}$, NR$^{10}$C(O)NR$^{11}$R$^{12}$, C(O)R$^{11}$, C(O)OR$^{11}$, and C(O)NR$^{11}$R$^{12}$;
each R$^7$, R$^8$ and R$^9$ is independently chosen from hydrogen, C$_{1-4}$ alkyl, C$_{3-6}$ cycloalkyl, and heterocycloalkyl and is optionally substituted with halo, hydroxy, C$_{1-3}$ alkyl, C$_{1-3}$ haloalkyl, and C$_{1-3}$ alkoxy; or any two of R$^7$, R$^8$ and R$^9$, together with the atom to which they are both attached can form a 3-7 membered cycloalkyl or heterocycloalkyl ring; and
each R$^{10}$, R$^{11}$ and R$^{12}$ is independently chosen from hydrogen, C$_{1-4}$ alkyl, C$_{3-6}$ cycloalkyl, and heterocycloalkyl and is optionally substituted with one or more groups chosen from halo, hydroxy and alkoxy; or any two of R$^{10}$, R$^{11}$ and R$^{12}$, together with the atom to which they are both attached, can form a 3-7 membered cycloalkyl or heterocycloalkyl ring.

2. The compound of claim 1, wherein R$^3$ is C$_{1-6}$ alkyl.

3. The compound of claim 2, wherein R$^3$ is methyl.

4. The compound of claim 1, of structural Formula (II):

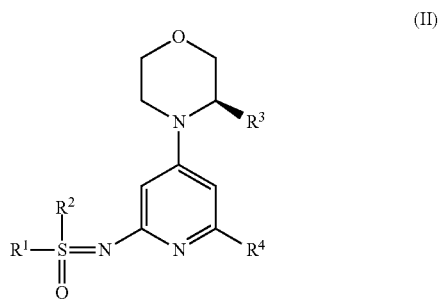

(II)

or a salt thereof, wherein:
R$^1$ and R$^2$ are independently chosen from C$_{1-4}$ alkyl, C$_{1-4}$ haloalkyl, C$_{3-6}$ cycloalkyl, C$_{3-6}$ heterocycloalkyl, aryl, and heteroaryl, each of which is optionally substituted with one or more R$^5$ groups, or R$^1$ and R$^2$, together with the sulfur to which they are both attached, form a heterocycloalkyl ring which is optionally substituted with one or more R$^5$ groups;
R$^3$ is chosen from hydrogen, C$_{1-6}$ alkyl, and C$_{1-6}$ haloalkyl;
R$^4$ is chosen from C$_{5-10}$ aryl and 5-10 membered heteroaryl and is optionally substituted with one or more R$^6$ groups;
each R$^5$ is independently chosen from NR$^8$R$^9$, halogen, cyano, hydroxy, oxo, alkyl, haloalkyl, cycloalkyl, heterocycloalkyl, hydroxyalkyl, OR$^8$, NR$^7$C(O)R$^8$, NR$^7$C(O)OR$^8$, NR$^7$C(O)NR$^8$R$^9$, C(O)R$^8$, C(O)OR$^8$, and C(O)NR$^8$R$^9$;
each R$^6$ is independently chosen from NR$^{11}$R$^{12}$, halogen, cyano, hydroxy, oxo, alkyl, haloalkyl, cycloalkyl, heterocycloalkyl, hydroxyalkyl, OR$^{11}$, NR$^{10}$C(O)R$^{11}$, NR$^{10}$C(O)OR$^{11}$, NR$^{10}$C(O)NR$^{11}$R$^{12}$, C(O)R$^{11}$, C(O)OR$^{11}$, and C(O)NR$^{11}$R$^{12}$;
each R$^7$, R$^8$ and R$^9$ is independently chosen from hydrogen, C$_{1-4}$ alkyl, C$_{3-6}$ cycloalkyl and heterocycloalkyl and is optionally substituted with halo, hydroxy, C$_{1-3}$ alkyl, C$_{1-3}$ haloalkyl and C$_{1-3}$ alkoxy; or any two of R$^7$, $R^8$ and $R^9$, together with the atom to which they are both attached can form a 3-7 membered cycloalkyl or heterocycloalkyl ring; and each $R^{10}$, $R^{11}$ and $R^{12}$ is independently chosen from hydrogen, $C_{1-4}$ alkyl, $C_{3-6}$ cycloalkyl and heterocycloalkyl and is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

5. The compound of claim 4, wherein $R^3$ is $C_{1-6}$ alkyl.

6. The compound of claim 5, wherein $R^3$ is methyl.

7. The compound of claim 6, wherein $R^4$ is 5-10 membered heteroaryl and is optionally substituted with one or more $R^6$ groups.

8. The compound of claim 7, wherein $R^4$ is chosen from indole, pyrrolopyridine, pyrazolopyridine, imidazolopyridine, pyrrolopyrazine, pyrazolopyrazine, pyrrolopyrimidine, pyrazolopyrimidine, imidazolopyrimidine, pyrrolopyridazine, pyrazolopyridazine, and imidazolopyridazine, and is optionally substituted with one or more $R^6$ groups.

9. The compound of claim 8, wherein $R^4$ is chosen from 1H-pyrrolo[2,3-b]pyridine, 7H-pyrrolo[2,3-c]pyridazine, 7H-pyrrolo[2,3-d]pyrimidine, and 5H-pyrrolo[2,3-b]pyrazine and is optionally substituted with one, two, or three $R^6$ groups.

10. The compound of claim 9, wherein $R^4$ is 1H-pyrrolo[2,3-b]pyridine and is optionally substituted with one or two $R^6$ groups.

11. The compound of claim 10, wherein each $R^6$ is independently chosen from $NR^{11}R^{12}$, halogen, cyano, hydroxy, oxo, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$.

12. The compound of claim 11, wherein each $R^6$ is independently chosen from $NR^{11}R^{12}$, halogen, cyano, hydroxy, and oxo.

13. The compound of claim 12, wherein $R^4$ is chosen from

[chemical structures]

14. The compound of claim 12, wherein $R^1$ and $R^2$ are independently chosen from $C_{1-4}$ alkyl, $C_{1-4}$ haloalkyl, $C_{3-6}$ cycloalkyl, $C_{3-6}$ heterocycloalkyl, aryl, and heteroaryl, each of which is optionally substituted with one or two $R^5$ groups, or $R^1$ and $R^2$, together with the sulfur to which they are both attached, form a heterocycloalkyl ring which is optionally substituted with one or more $R^5$ groups;

each $R^5$ is independently chosen from $NR^8R^9$, halogen, cyano, hydroxy, oxo, alkyl, haloalkyl, cycloalkyl, heterocycloalkyl, hydroxyalkyl, $OR^8$, $NR^7C(O)R^8$, $NR^7C(O)OR^8$, $NR^7C(O)NR^8R^9$, $C(O)R^8$, $C(O)OR^8$, and $C(O)NR^8R^9$.

15. The compound of claim 14, wherein each $R^5$ is independently chosen from alkyl, haloalkyl, cycloalkyl, heterocycloalkyl, hydroxyalkyl, $OR^8$, $NR^7C(O)R^8$, $NR^7C(O)OR^8$, $NR^7C(O)NR^8R^9$, $C(O)R^8$, $C(O)OR^8$, and $C(O)NR^8R^9$.

16. The compound of claim 15, wherein each $R^5$ is independently chosen from $C(O)R^8$, $C(O)OR^8$, and $C(O)NR^8R^9$.

17. The compound of claim 16, wherein $R^1$ and $R^2$ are independently chosen, aryl, and heteroaryl and $C_{1-4}$ alkyl, $C_{1-4}$ haloalkyl, $C_{3-6}$ cycloalkyl, $C_{3-6}$ heterocycloalkyl, aryl, and heteroaryl and are optionally substituted with one or two $R^5$ groups.

18. The compound of claim 17, wherein $R^1$ and $R^2$ are independently chosen from $C_{1-4}$ alkyl, $C_{1-4}$ haloalkyl, $C_{3-6}$ cycloalkyl, $C_{3-6}$ heterocycloalkyl and are optionally substituted with one or two $R^5$ groups.

19. The compound of claim 17, wherein $R^1$ and $R^2$ are independently chosen from $C_{1-4}$ alkyl and $C_{3-6}$ cycloalkyl.

20. The compound of claim 17, wherein $R^1$ and $R^2$, together with the sulfur to which they are both attached, forms a heterocycloalkyl ring and is optionally substituted with one or two $R^5$ groups.

21. The compound of claim 1, wherein the structure is chosen from

[chemical structure]

-continued
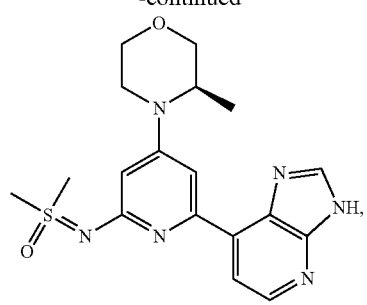
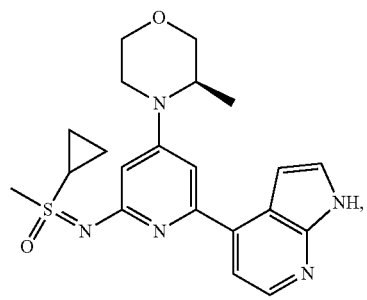
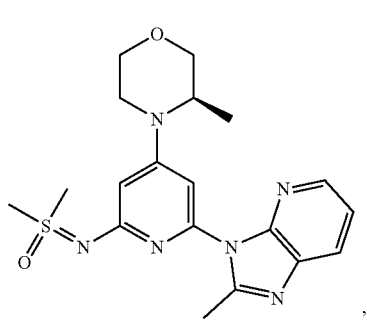
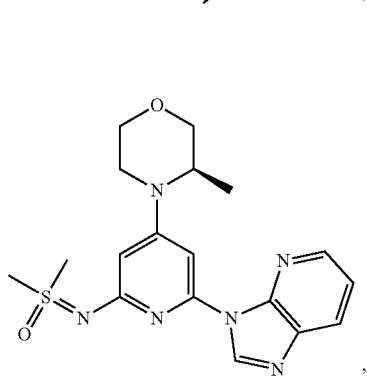
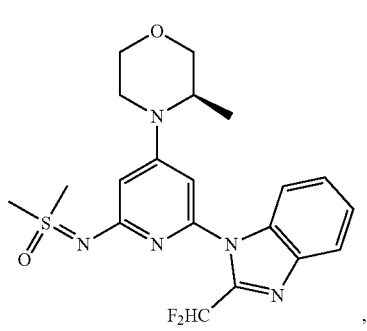
-continued
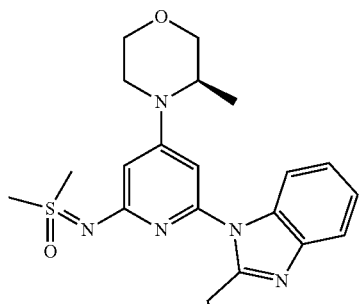
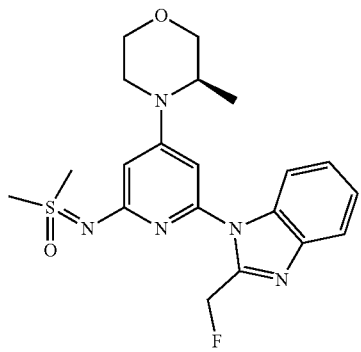
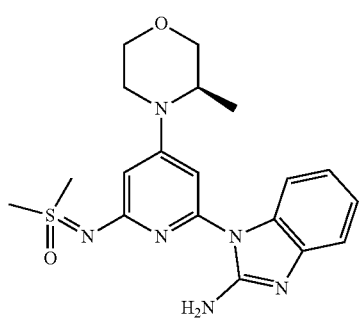
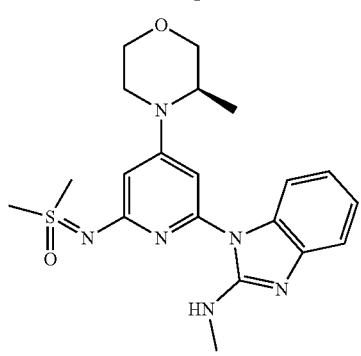
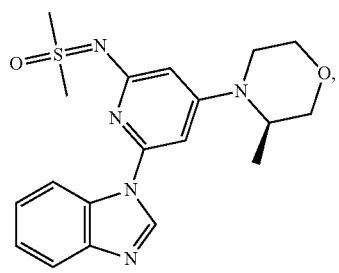

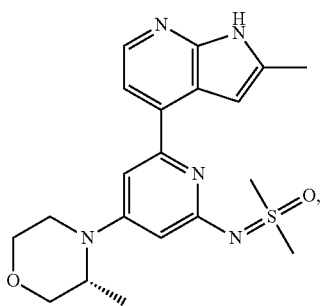
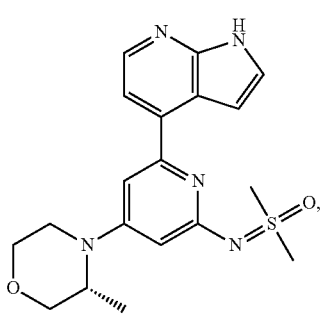
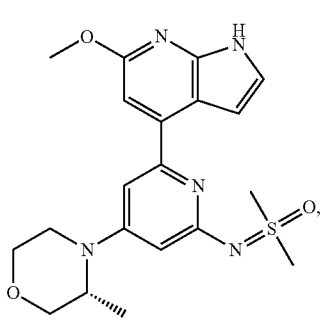
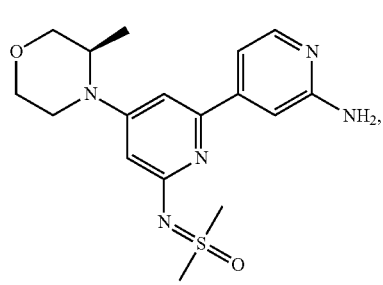
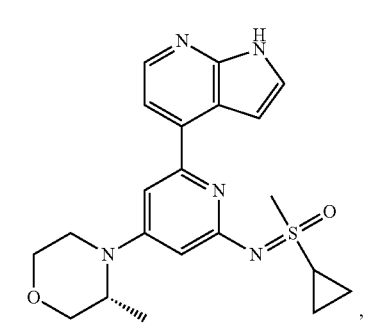
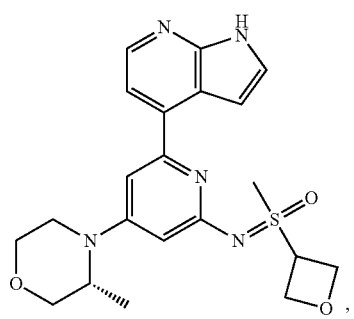
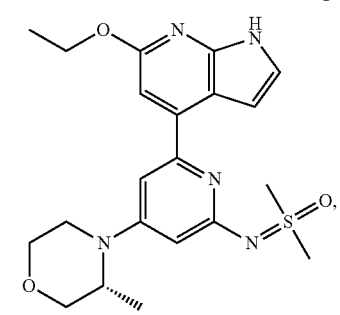
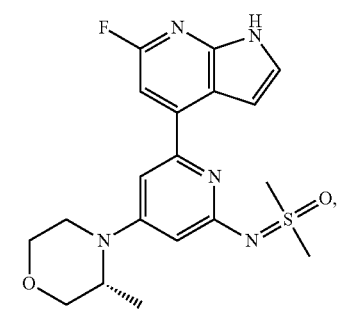
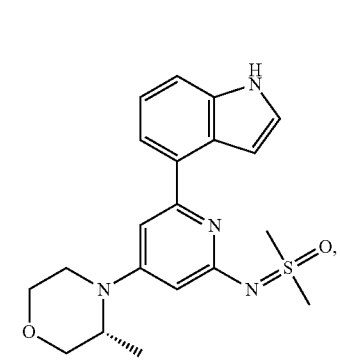
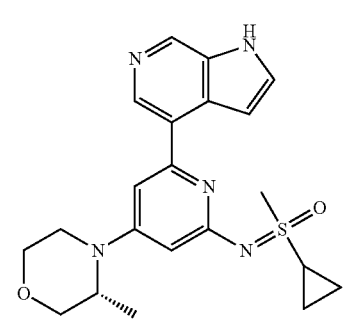

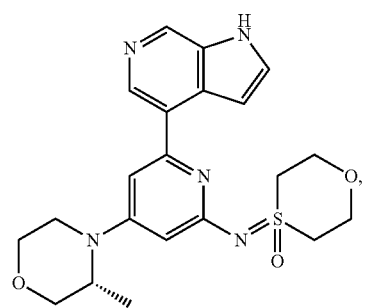
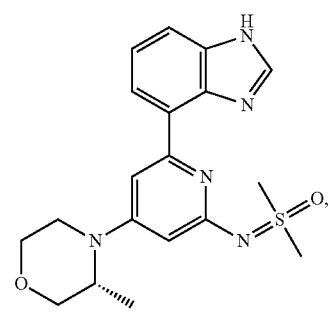
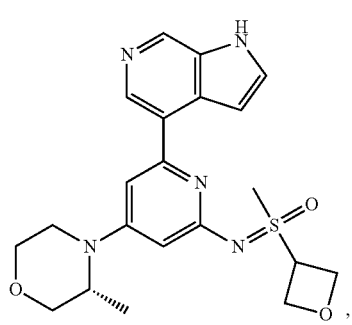
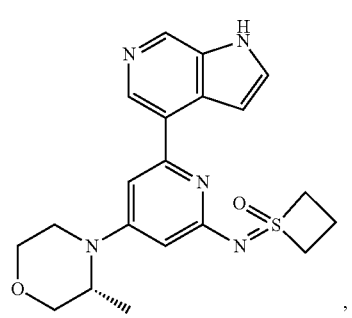
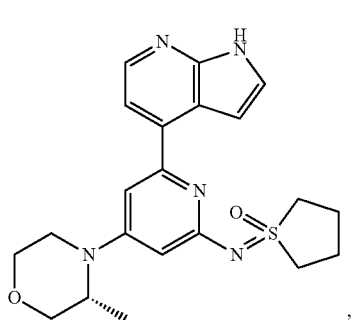
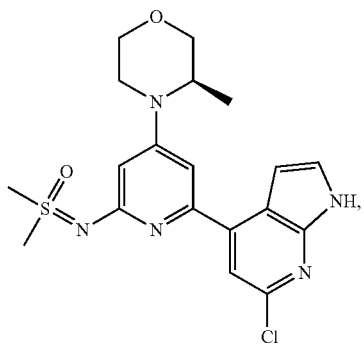
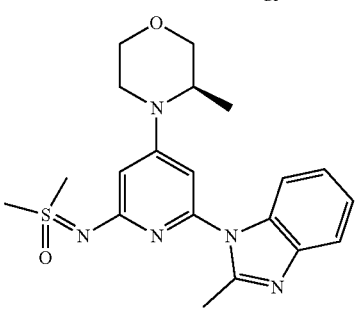
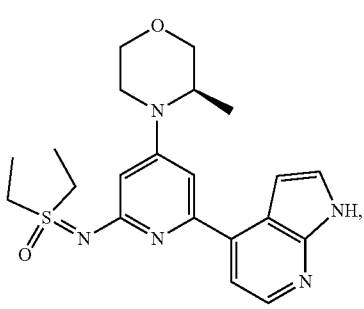
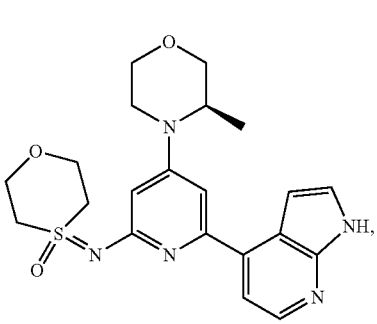
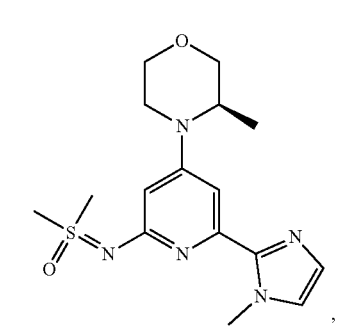

-continued
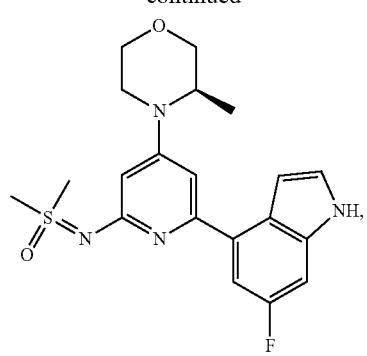
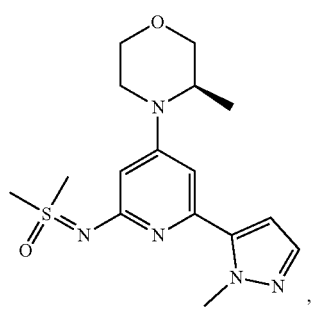
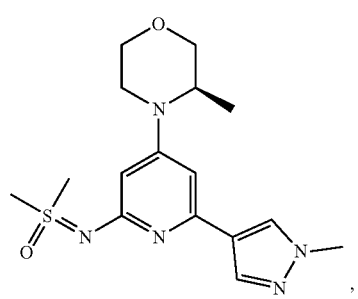
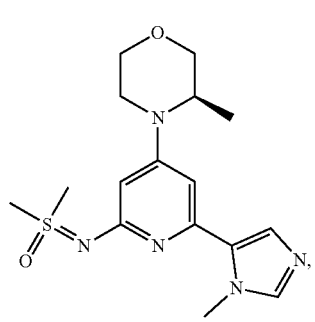
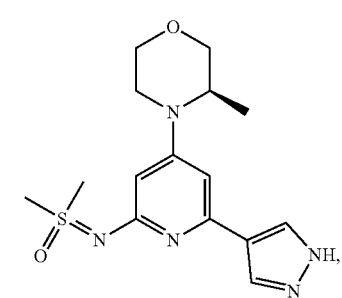
-continued
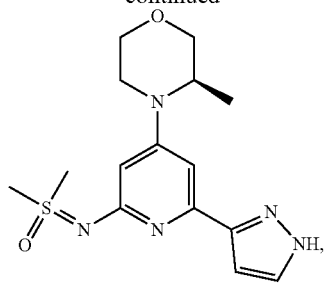
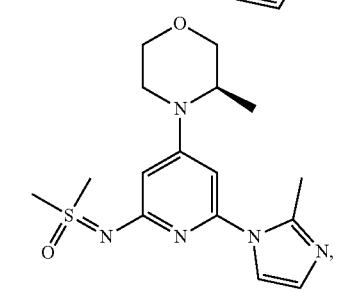
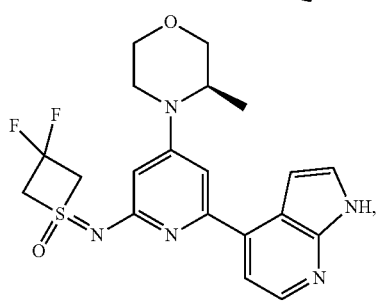
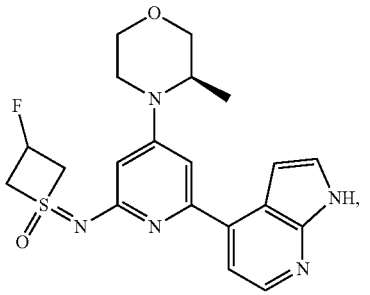
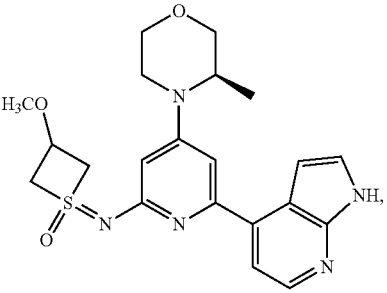

-continued

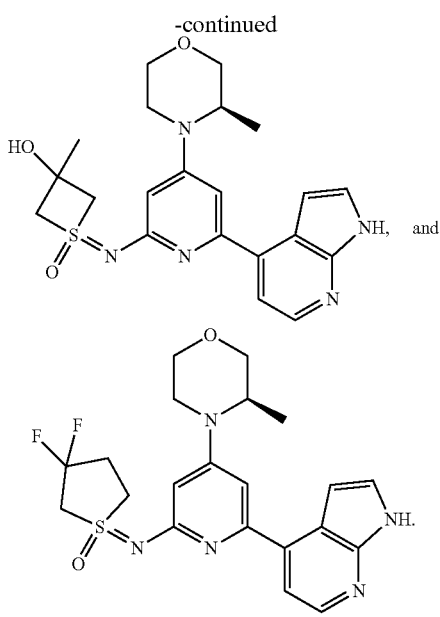

22. A pharmaceutical composition comprising a compound of claim 1 together with a pharmaceutically acceptable carrier.

23. A method of sensitizing cells to DNA-damaging agents comprising administering to a patient a compound of claim 1.

24. A method of preventing cell repair from DNA damage comprising administering to a patient a compound of claim 1.

25. A method of inhibiting ATR kinase comprising contacting ATR kinase with a compound of claim 1.

26. A method of treating an ATR kinase-mediated disease chosen from a proliferative disease, a myeloproliferative disorder, and cancer, comprising administrating a therapeutically effective amount of a compound of claim 1 to a patient having said disease.

27. A method of increasing the sensitivity of cancer cells to a cancer therapy chosen from chemotherapy or radiation therapy by administering to a patient a compound of claim 1.

28. A method for achieving an effect in a patient comprising administering a therapeutically effective amount of a compound of claim 1 to a patient, wherein the effect is increased sensitivity to chemotherapy agents.

29. The method as recited in claim 26, wherein the ATR kinase-mediated disease is a proliferative disease.

30. The method as recited in claim 26, wherein the ATR kinase-mediated disease is a myeloproliferative disorder.

31. The method as recited in claim 26, wherein the ATR kinase-mediated disease is cancer.

32. The method as recited in claim 31, wherein the cancer is chosen from lymphoma and pancreatic cancer.

* * * * *